(12) United States Patent
Goldberg et al.

(10) Patent No.: US 8,165,893 B1
(45) Date of Patent: Apr. 24, 2012

(54) MEDICAL MONITORING AND COORDINATED CARE SYSTEM

(75) Inventors: Jason Goldberg, Ontario (CA); Thomas C. Beckerman, Ontario (CA)

(73) Assignee: Ideal Life Inc., Toronto (CA)

( * ) Notice: Subject to any disclaimer, the term of this patent is extended or adjusted under 35 U.S.C. 154(b) by 1089 days.

(21) Appl. No.: 11/356,739

(22) Filed: Feb. 16, 2006

Related U.S. Application Data

(60) Provisional application No. 60/653,653, filed on Feb. 16, 2005.

(51) Int. Cl.
*G06Q 50/00* (2012.01)
(52) U.S. Cl. .................................. 705/2; 705/3
(58) Field of Classification Search ............ 705/2–3
See application file for complete search history.

(56) References Cited

U.S. PATENT DOCUMENTS

| | | | |
|---|---|---|---|
| 4,731,726 A | 3/1988 | Allen, III | |
| 5,390,238 A | 2/1995 | Kirk et al. | |
| 5,576,952 A | 11/1996 | Stutman et al. | |
| 5,704,366 A | 1/1998 | Tacklind et al. | |
| 5,772,586 A | 6/1998 | Heinonen et al. | |
| 5,822,715 A | 10/1998 | Worthington et al. | |
| 5,827,180 A | 10/1998 | Goodman | |
| 5,832,448 A | 11/1998 | Brown | |
| 5,879,375 A * | 3/1999 | Larson et al. | 607/30 |
| 5,897,493 A | 4/1999 | Brown | |
| 5,956,501 A | 9/1999 | Brown | |
| 5,997,476 A | 12/1999 | Brown | |
| 6,024,699 A | 2/2000 | Surwit et al. | |
| 6,050,940 A | 4/2000 | Braun et al. | |
| 6,101,478 A | 8/2000 | Brown | |
| 6,168,563 B1 | 1/2001 | Brown | |
| 6,196,970 B1 | 3/2001 | Brown | |
| 6,221,010 B1 | 4/2001 | Lucas | |
| 6,233,539 B1 | 5/2001 | Brown | |
| 6,246,992 B1 | 6/2001 | Brown | |
| 6,248,065 B1 | 6/2001 | Brown | |
| 6,270,455 B1 | 8/2001 | Brown | |
| 6,302,844 B1 | 10/2001 | Walker et al. | |
| 6,368,273 B1 | 4/2002 | Brown | |
| 6,375,614 B1 | 4/2002 | Braun et al. | |
| 6,379,301 B1 | 4/2002 | Worthington et al. | |
| 6,381,577 B1 | 4/2002 | Brown | |
| 6,454,705 B1 | 9/2002 | Cosentino et al. | |

(Continued)

OTHER PUBLICATIONS

Robinson, Brian. "VA improves telehealth access", Federal Computer Week. Falls Church: Jan. 7, 2002. vol. 16, Iss. 1; p. 30.*

*Primary Examiner* — Robert Morgan
*Assistant Examiner* — Robert Sorey
(74) *Attorney, Agent, or Firm* — Frank J. DeRosa; Frommer Lawrence & Haug LLP

(57) ABSTRACT

Systems and methods are provided for monitoring members of a group and providing coordinated care of the members. Monitoring devices are provided to each of the members which may take periodic health measurements of the member. The health measurement is compared to intervention criteria, which when satisfied, cause one or more interventions to be provided, such as a message sent to a member, a message sent to a health care provider or other interested individual, medical care provided to the member, or other intervention. Monitoring devices may be provided on a subscription basis. Group membership can be dynamic and based on a member's current health measurements. Health measurement information may be provided in reports.

9 Claims, 19 Drawing Sheets

U.S. PATENT DOCUMENTS

| | | |
|---|---|---|
| 6,589,169 B1 | 7/2003 | Surwit et al. |
| 7,024,369 B1 * | 4/2006 | Brown et al. ............... 705/2 |
| 2002/0016719 A1 * | 2/2002 | Nemeth et al. ............. 705/2 |
| 2002/0065682 A1 * | 5/2002 | Goldenberg ................ 705/2 |
| 2002/0198663 A1 * | 12/2002 | Lau et al. .................. 702/19 |
| 2003/0009356 A1 * | 1/2003 | Hildebrand et al. ........ 705/2 |
| 2003/0212579 A1 * | 11/2003 | Brown et al. ............... 705/2 |
| 2003/0233250 A1 * | 12/2003 | Joffe et al. ................. 705/2 |
| 2004/0019259 A1 * | 1/2004 | Brown et al. ............ 600/300 |
| 2004/0034288 A1 * | 2/2004 | Hennessy et al. ....... 600/300 |
| 2004/0059599 A1 | 3/2004 | McIvor |
| 2004/0102683 A1 | 5/2004 | Khanuja et al. |
| 2004/0116785 A1 * | 6/2004 | Bulat ...................... 600/300 |
| 2004/0210458 A1 * | 10/2004 | Evans et al. ................ 705/2 |
| 2004/0230127 A1 * | 11/2004 | Bardy ..................... 600/509 |
| 2004/0254816 A1 * | 12/2004 | Myers ......................... 705/2 |
| 2005/0137481 A1 * | 6/2005 | Sheard et al. ........... 600/508 |
| 2005/0144042 A1 * | 6/2005 | Joffe et al. ................. 705/2 |
| 2007/0135724 A1 * | 6/2007 | Ujhazy et al. ........... 600/529 |

* cited by examiner

Welcome LeeAnn

Select Role ▶ Professional

My Patients

Please select a Group:  Please select a Project Phase:

All Patients  Phase 1

Submit

| Name | Alerts | This Week Interactions | Address | Physician |
|---|---|---|---|---|
| ABCPatient1, Test | | 0 | 101 Main Street Los Angeles, CA, 95000 | Doctor, Test Phone: 3232628000 |
| ABCPatient2, Test | | 1 | 102 Main Street Los Angeles, CA, 95000 | Doctor, Test Phone: 3232628001 |

Page 1 of 1 (2 record(s) found)

◄◄ ◄ ► ►►

About this site   Privacy Policy   Terms of Use (c) 2003 - 2005 IDEAL LIFE Inc., All Rights Reserved.

Fig. 4

Welcome LeeAnn

Select Role ▶

Interactions

Please select the Interaction type:

Active patient alerts 

To create new Interaction click here.
To view an existing Interaction click on the DATE below.

| Date/MEDIC Code | Duration | Type | Patient | Alerts |
|---|---|---|---|---|
| 2/9/2005 5:22:00 AM | | Call to patient | Test ABCPatient2 | |
| Purple Zone Alert threshold reading | | | | |
| Purple Zone Alert Followup - Systolic less than 100 or diastolic less than 60. - BP:98/73 HR:72 Feb/08/2005 09:19:11 PM | | | | |
| 2/9/2005 5:22:36 AM | | Call to PCP | Test ABCPatient2 | |
| Purple Zone Alert threshold reading | | | | |
| Purple Zone Alert Followup - Systolic less than 100 or diastolic less than 60 - Call PCP (IF PCP UNAVAILABLE ENSURE PATIENT IS SEEN BY HOSPITALIST IN CCC OR ER). - BP:98/73 HR:72 Feb/08/2005 09:19:11 PM | | | | |

Page 1 of 1 (2 record(s) found)

About this site    Privacy Policy    Terms of Use (c) 2003 - 2005 IDEAL LIFE Inc., All Rights Reserved.

Fig. 6

Welcome LeeAnn | Sign Out | Home

Select Role ▸ Professional | ~~~~~~

Patient Summary for -

Please select the patient you would like to view:

| Select Patient | ▼ | Submit |

Alerts   Readings   Office BP   Medications   Pharmacy   Reports

Interactions

◉ Not Completed   ◉ Completed   ◉ All   Select

To view Not Completed Interactions click on the DATE below.

No records found!

Enter a new Interaction below:

| Select Physician | Date (mm/dd/yyyy) | Time (hh:mm am/pm) |
| LeeAnn | | |

| Select Interaction Type | Duration (hh:mm) | MEDIC Code |
| Select Interaction Type | | |

Select Interaction Purpose      Comment (Type CTRL-D to datestamp)

| Select Interaction Purpose | |

Selected Purposes:

Submit

About this site    Privacy Policy    Terms of Use (c) 2003 - 2005 IDEAL LIFE Inc., All Rights Reserved.

Fig 7

Welcome LeeAnn

Select Role ▸ Professional

Edit Interaction or Alert

Test ABCPatient2
102 Main Street
Los Angeles, 43, 95000
Phone: 3232628001

Current Physician: Test Doctor
110 Pharmacy Rd
Los Angeles, 43, 95000
Phone: 3232628003

| Select Physician | Date (mm/dd/yyyy) | Time (hh:mm am/pm) |
|---|---|---|
| LeeAnn | 2/9/2005 | 05:22 am |

| Select Interaction Type | Duration (hh:mm) | MEDIC Code |
|---|---|---|
| Update records | | |

Select Interaction Purpose: Select Interaction Purpose

Comment (Type CTRL-D to datestamp):
Enter the outcome(s) of the earlier alert - visit/admission/medication etc.

Selected Purposes:
Record PCP office visit details
Record symptoms/side effects
Record medication change
Record diet change
Record hospital visit
Record hospital admission Completed  Alert:

Submit

About this site    Privacy Policy    Terms of Use (c) 2003 - 2005 IDEAL LIFE Inc., All Rights Reserved.

Fig. 8

Welcome LeeAnn

Select Role ▸ Professional | Consumer

Patient Summary for Test ABCPatient2 - Phase 1

Please select the patient you would like to view:

| ABCPatient2, Test | | Submit |

102 Main Street
Los Angeles, CA, 95000
Phone: 3232628001

Current Physician: Doctor, Test
110 Pharmacy Rd
Los Angeles, CA, 95000
Phone: 3232628003

Alerts   Interactions   Readings   Medications   Pharmacy   Reports

Office BP

No records found!

Enter a new Office BP reading below:

| Systolic | Diastolic | Heartrate | Date(mm/dd/yyyy) | Physician |
|----------|-----------|-----------|------------------|-----------|
|          |           |           |                  | Select Physician |

Submit

About this site   Privacy Policy   Terms of Use (c) 2003 - 2005 IDEAL LIFE Inc., All Rights Reserved.

Fig. 9

Latest 150 Readings (Max.)

| Systolic | Diastolic | Heart Rate | Reading Date |
|---:|---:|---:|---|
| 129 | 81 | 68 | 2/10/2005 9:13:50 PM |
| 110 | 72 | 63 | 2/10/2005 1:02:28 AM |
| 98 | 73 | 72 | 2/9/2005 1:19:11 PM |
| 119 | 74 | 72 | 2/9/2005 12:11:12 PM |
| 132 | 80 | 64 | 2/8/2005 8:37:01 PM |
| 129 | 80 | 62 | 2/8/2005 12:39:46 PM |
| 117 | 73 | 67 | 1/1/2004 4:22:09 PM |
| 128 | 81 | 70 | 1/1/2004 4:12:07 PM |
| 125 | 77 | 65 | 1/1/2004 4:06:08 PM |

About this site    Privacy Policy    Terms of Use (c) 2003 - 2005 IDEAL LIFE Inc., All Rights Reserved.

FIG. 10b

Confidential

FAX

2/11/2005 11:18:24 PM
To: Test Doctor
Fax:
From: LeeAnn
Subject:      Hypertension      Report

Patient

Review

Attached

This document may contain confidential and privileged information. If you are not the intended recipient, please notify the sender immediately, and destroy this document and any copies made. Any dissemination or use of this information by a person other than the intended recipient is unauthorized and may be illegal. Unless otherwise stated, opinions expressed in this document are those of the author and are not endorsed by the author's employer.

Fig. 12 a

Confidential  2/11/2005 11:18:24 PM

Hypertension Project Report

Patient:
Test ABCPatient1
101 Main Street
Los Angeles, CA, 95000
Phone: 3232628000

Member ID: 1

Physician:
Test Doctor
110 Pharmacy Rd
Los Angeles, CA, 95000
Phone: 3232628003

Physician ID: 1

Summary - Date start: 2/1/2005    Date end: 2/10/2005

|  | MEAN | MIN | MAX |
|---|---|---|---|
| Systolic | 121 | 110 | 132 |
| Diastolic | 73 | 62 | 83 |
| Pulse Pressure | 48 | 39 | 57 |
| MAP (Mean Arterial Pressure) | 89 | 78 | 96 |
| Heart Rate | 73 | 68 | 78 |

Percent of systolic readings above limits: 0.00%

Percent of systolic readings below limits: 100.00%

Percent of diastolic readings above limits: 0.00%

Percent of diastolic readings below limits: 100.00%

Fig. 12b

Confidential  2/11/2005 11:18:24 PM

Medications
No records found!

Pharmacy
No records found!

Fig.12

Confidential 2/11/2005 11:18:24 PM

Daily Systolic & Diastolic Readings

Daily Heart Rate Readings

Confidential  2/11/2005 11:18:25 PM

Daily Average Readings

| Date | Systolic | Diastolic | Heart rate |
|---|---|---|---|
| 2/1/2005 | | | |
| 2/2/2005 | | | |
| 2/3/2005 | | | |
| 2/4/2005 | | | |
| 2/5/2005 | 125 | 68 | 73 |
| 2/6/2005 | | | |
| 2/7/2005 | | | |
| 2/8/2005 | 126 | 76 | 70 |
| 2/9/2005 | 116 | 68 | 73 |
| 2/10/2005 | 122 | 80 | 77 |

Fig. 12P

Confidential

All Readings To Date

| Date | Systolic | Diastolic | MAP | Pulse Pressure |
|---|---|---|---|---|
| 2/5/2005 4:28:46 AM | 125 | 68 | 87 | 57 |
| 2/8/2005 12:49:32 PM | 132 | 78 | 96 | 54 |
| 2/8/2005 9:16:47 PM | 120 | 75 | 90 | 45 |
| 2/9/2005 11:06:02 AM | 115 | 64 | 81 | 51 |
| 2/9/2005 11:14:51 AM | 110 | 62 | 78 | 48 |
| 2/9/2005 7:47:58 PM | 125 | 80 | 95 | 45 |
| 2/10/2005 11:27:56 AM | 123 | 78 | 93 | 45 |
| 2/10/2005 9:36:28 PM | 122 | 83 | 96 | 39 |

Fig. 12 g

MEDICAL MONITORING AND COORDINATED CARE SYSTEM

PRIORITY CLAIM

This application claims the benefit of U.S. provisional application No. 60/653,653 titled MEDICAL MONITORING AND COORDINATED CARE SYSTEM, filed Feb. 16, 2005, which is incorporated herein by reference in its entirety.

RELATED APPLICATIONS

This application is related to the following U.S. patent applications, the disclosures of each of which is incorporated herein by reference:

U.S. patent application Ser. No. 09/075,097, titled MEDICAL MONITORING SYSTEM AND DEVICE, filed Oct. 11, 2001 (now U.S. Pat. No. 6,840,904);

U.S. patent application Ser. No. 10/963,205, titled MEDICAL MONITORING/CONSUMABLES TRACKING DEVICE, filed Oct. 11, 2004;

U.S. Provisional Patent Application Ser. No. 60/487,471, titled MEDICAL MONITORING/CONSUMABLES TRACKING DEVICE, filed Jul. 15, 2003;

U.S. patent application Ser. No. 10/892,520, titled MEDICAL MONITORING/CONSUMABLES TRACKING DEVICE, filed Jul. 15, 2004;

U.S. Provisional Patent Application Ser. No. 60/493,904, titled PERSONAL HEALTH MANAGEMENT DEVICE, METHOD AND SYSTEM, filed Aug. 7, 2003;

U.S. patent application Ser. No. 10/913,140, titled PERSONAL HEALTH MANAGEMENT DEVICE, METHOD AND SYSTEM, filed Aug. 6, 2004;

U.S. Provisional Patent Application Ser. No. 60/562,876, titled MEDICAL MONITORING SYSTEM, filed Apr. 16, 2004;

U.S. patent application Ser. No. 11/108,355, titled PERSONAL HEALTH MONITORING AND/OR COMMUNICATION SYSTEM, filed Apr. 18, 2005; and U.S. patent application Ser. No. 10/868,676, titled MEDICAL MONITORING SYSTEM AND DEVICE, filed Jun. 15, 2004.

BACKGROUND OF THE INVENTION

The present invention relates to managing health care to be provided to members of a group, e.g., managed health care plans, groups and organizations such as HMOs, group health insurance plans (HIPs), medical groups, and to individuals who may wish to manage health care. More particularly, the invention relates to identifying and/or monitoring members of the group based on the state of health of members, e.g., actual or possible high blood pressure, actual or possible high blood cholesterol, actual or possible diabetes, actual or possible severe obesity, etc., and managing health care provided to such members based on measurements, e.g., physiological measurements, made on the members. The invention contemplates the use of devices to provide at least some of the measurements which can operate out of a health care provider's or professional's facility, e.g., such devices may be portable and carried by members and/or used in members' homes or places of business.

SUMMARY OF THE INVENTION

An embodiment of the present invention provides methods, systems, software, user interfaces and devices for managing health care to be provided to a group of members so as to identify and/or monitor members actually or possibly in need of care, and seeking to provide such care before more serious or more expensive care is needed. In this embodiment, members are identified for monitoring based on data such as medical history and/or initial measurements related to one or more medical conditions such as high blood pressure. Measurements are taken on such members and provided to a database. The database processes the measurements and provides data which indicates, or from which can be determined, a need for health care. Members in such need are notified of the need. Such members may be encouraged to obtain the health care and/or arrangements may be made to provide such members with the health care.

Embodiments of the invention contemplate using devices operated without the aid of health care or other professionals, e.g., a portable device which a member carries, or a device which a member uses at home or a place of business, operated by a member, or automatically, etc. Measurements may also be taken in facilities of health care providers. Measurement data and other information may be electronically provided to the database via a network, communications system, intranet, Internet, e.g., a cell phone system, radio system, PSTS or POTs telephone systems, paging systems, satellite systems, etc. Examples of such devices and systems are disclosed in the referenced patent applications and/or are known in the prior art.

Embodiments of the invention contemplate that such groups provide for and/or arrange health care for members by health care professionals such as doctors, where the group may be responsible for paying the health care professions for the health care service and the group charges or is paid on a per member basis. Such arrangements are known in the prior art. Such an arrangement may, for example, encourage groups to deliver the health care services at an aggregated cost that is low compared to the aggregated amounts paid to the groups. For example, fees to be paid to professionals may be pre-agreed for given health care services, and equal or substantially equal fees may be charged to all or some members of the group.

The invention disclosed herein allows groups such as those described herein to identify members who may be in need of health care, and to detect at an early stage when such health care should be provided so as to present the possibility that less expensive health care can be provided early to avoid the need to provide more extensive and correspondingly more expensive health care later. In an embodiment of the invention, health care practitioners, e.g., practitioners other than medical doctors such as nurses, medical assistants, paramedics, trained staff, may determine when to intervene and encourage or arrange for health care to be provided to monitored members by appropriate health care professionals.

As a business model, a service provider may provide all or some of the hardware and software needed to perform the monitoring, data acquisition, data storage, data processing, etc., to a group on a per member subscription basis. According to this model, the group factors into its charges to members the cost of the per member subscription and/or the projected savings to the group from identification and early intervention of members needing health care services. This model may also provide for the group underwriting the cost of devices used by members, so that the service provider avoids the need for a high capital investment for each group that the service provider serves. In this model, the service provider provides, maintains and operates a database (and associated communication protocols, data acquisition and access, etc.) which is used to service a plurality of groups. In one embodiment, the service provider may opt to provide the devices free or at low cost, and amortize the cost of the devices over the term of a contract with a group. This provides a steady income stream after initial delivery of the devices, much as a razor company or computer printer company charges a low price for a razor or printer with the expectation that razors and ink will be purchased from the company over the life of the razor or printer.

Embodiments of the invention described below provide for enrollment of members, identifying members to be monitored, data acquisition from members by remote devices and/or from measurements made in health care professionals' facilities, processing of data to form groups of members with like medical conditions and/or degrees of seriousness of a medical condition, and/or to identify candidates for intervention, e.g., by means of automatically generated alerts, and/or to notify such members and/or health care professionals attending to such members, etc.

For example, embodiments of the invention may obtain and/or monitor physiologic and other information, such as, but not limited to, blood pressure, heart rate, body temperature, weight, EKG, EEG, glucose level (blood sugar), respiratory capacity (PEAK flow), substances and/or chemical presence or level (e.g., drugs, proteins, hormones, compounds, chemicals and things which may be found in a member's body, blood, body fluids, etc.), therapeutic effect, efficacy, compliance, etc. Although the present invention may be described by way of example in relation to certain types of information and monitoring, the invention is generally applicable to many types information and monitoring.

Monitoring devices may be portable and may be easily worn (e.g., on a wrist, belt, etc.) or carried (e.g., in a pocket, pocketbook, etc.). Transmission devices may be stationary, and may be placed in any convenient location in a home, office, play or exercise facility. Monitoring devices and an associated transmission device may be located in a same building or sub-part of a building (e.g., a house, a room in a building, an apartment in a building, an office in building, etc.). In this respect, a monitored member may move freely about the building and information will be transmitted between monitoring devices and a transmission device. A monitored member may locate a monitoring device 10, such as a scale, in one room and the transmission device in another, e.g., convenient to a communications port (telephone jack, internet terminal, etc.).

The specific type of monitoring device is not critical, and any suitable monitoring device, communication protocol, network may be used. A member and/or a health care professional may be notified or provided with information as described herein or in any suitable manner, e.g., telephone, pager, fax, Internet, mail, etc.

As mentioned, in an embodiment of the invention the system includes a database for storing member information and other information, as well as at least an associated computer. The computer may receive information from and provide information to monitoring devices, and may also provide information to and receive information from health care providers, family members, etc. As mentioned, the computer may provide and/or receive such information over a network, e.g., the Internet.

The computer may be involved with the health and medical condition of individual members, health and medical conditions in general, and/or drug tests, clinical evaluations, etc. Thus, the computer can collect information from individual members, and analyze and process such information in the nature of a health-related database for a specific health issue or condition. Information may be provided, e.g., for research, analysis or other purposes stripped of personal patient information. Where a monitoring device includes an input device, members may enter demographic information and other information that may be included, e.g., with other member information for, e.g., analysis and research purposes.

Member information may also be used by the computer for targeted messages, e.g., free text or other messages, health related news, alerts, advertising, etc. For example, where a monitoring device supplies blood pressure information, the information may be used to identify a member as a candidate for a hypertension drug, etc. Similarly, such a member may be supplied with an alert of an environmental condition, such as extreme high or low temperatures, or ozone content using member position or geographical information. A monitoring device that supplies respiratory information may identify the associated member as a candidate for an alert of high ozone content, or high air pollution levels, etc.

The computer may also provide an interface for use in providing coordinated care for one or more or a group of individuals being monitored with the monitoring device. The interface preferably provides information to a care-coordinator in a manner for the coordinator to act appropriately in a proactive manner. This may be accomplished, for example, by generating alerts for the coordinator based on physiologic measurements and/or action items for the coordinator based on the alerts.

With respect to compliance, the user interface of a monitoring device may be used to provide and receive compliance-related information.

In one embodiment, a method for managing health care made available to a group of people is provided in which initial physiological measurement data related to each of a plurality of people in the group is received. In general, the group of people may be any group of people, such as members of a managed health care organization, members of a fitness organization, members of an institution, all citizens of a state or country, all members of a family, or other group. The physiologic measurement data may be any data indicating a physiologic, health or other condition or state of an individual. Initial measurements may be received to provide a baseline health condition of the person. Additional physiological measurement data related to each person in a sub-group of the group of people may be received. In general, the persons in the sub-group have an initial physiological measurement that satisfies a criterion, such as a first criterion, which may be value. A computing device may be used to automatically determine that the initial physiologic measurement satisfies the first criterion. For example, a sub-group of a group of persons may be created for individuals having a blood pressure measurement above or below a certain initial criteria. The additional physiological measurement data may be obtained using a portable device, such as a medical monitoring device that is provided to each person in the sub-group. The additional physiological measurement may relate to the sub-group, such as in the example above, additional blood pressure readings, or other physiological measurement. The additional monitoring may be received according to a frequency or period as necessary for the sub-group. Additional monitoring may be based on a treatment regimen that is appropriate for the sub-group.

Each person in the sub-group may be contacted when an additional physiological measurement data obtained by a portable device satisfies a second criterion, which may be a value, such as a higher or lower reading than the initial first criterion. A computing device may be used to automatically determine that the initial physiologic measurement satisfies the second criterion. The additional physiological measurements, when compared to a first and second criterion may provide an indication of a change in a person's health, physical or physiological condition. The person, or representative or other contact, may be contacted in connection with the reading. The contacting may be via an electronically delivered message, such as a text message sent to a portable device, email, voicemail or other message, or a telephone call from a health care manager or other individual associated with providing managed health care. Prior to the contact, an individual, such as a health care provider, care coordinator, health care professional, such as a nurse, doctor, physician's assistant, or other interested individual may review the additional physiologic measurement that satisfies the second criterion, or other additional physiologic measurement, e.g., to ensure that intervention is appropriate. In general, the method may be provided by health care practitioners, which may include doctors, but is typically provided by a nurse, physician's assistant or other health care provider or professional.

In another embodiment, a method for managing health care is provided in which initial physiologic measurement data related to each of a plurality of people may be received. Additional physiological measurement data related to each person in a group of the plurality people whose related or associated initial physiological measurement data satisfies at least one first criterion obtained using a portable device provided to each person in the group may also be received. Each person in the group whose additional physiological measurement data obtained by a portable device satisfies at least one second criterion, may be contacted in connection with the additional physiological measurement data satisfying the at least one second criteria.

In another embodiment, a method for managing health care made available to a group of people is provided in which initial physiologic measurement data related to a potential health-related concern from each of a plurality of people in the group may be received. In general, health-related concerns can be for example related to blood pressure, weight, respiratory flow volumes, cholesterol, blood insulin levels, or other health condition. Additional physiological measurement data related to the potential health concern may be received from each person in a sub-group of the plurality of people whose related initial physiological measurement data satisfies at least one first criterion obtained using a portable device provided to each person in the sub-group. Each person, or representative or other contact, in the sub-group whose additional physiological measurement data obtained by a portable device satisfies at least one second criterion indicating that the potential health-related concern is an actual health-related concern, may be contacted in connection with the additional physiological measurement data satisfying the at least one second criteria and informing of the actual health-related concern. The actual health-related concern may be an indication that a person's physiological measurement has changed, for example, to the extent that treatment or intervention is necessary.

In another embodiment, a method for managing health care made available to a group of people is provided in which an initial physiologic measurement data related to a potential health-related concern from each of a plurality of people in the group may be received. With the aid of a computing device, a person may be identified for a sub-group of the plurality of people, each identified person having related initial physiological measurement data that satisfies at least one first criterion. Each person in the sub-group may be provided a portable device capable of providing additional physiological measurement data related to the potential health concern. The additional physiological measurement data from each person in the sub-group may be received and the additional physiological measurement may be obtained using the portable device provided to each person in the sub-group.

A plurality of second criteria may be established, each of which indicates at a different level that the potential health concern is an actual concern. For example, criteria may be established at one or more thresholds which indicate that a physiological measurement may be problematic or cause concern. In one example, for a sub-group relating to blood pressure, one or more criteria may be established in which, an intervention may be taken, such as a somewhat elevated blood pressure level, a lower than normal and potentially unsafe blood pressure level, or an emergency or high blood pressure level. Different levels of intervention may be associated with each of the plurality of second criteria. For example, for a slightly elevated blood pressure measurement, a message may be sent asking a person whether medication was missed, for a lower than normal blood pressure measurement, a call may be made to an individual to determine whether something out of the ordinary had occurred, and for a dangerously high blood pressure level, 911 or other emergency service may be called, or other appropriate intervention. A computing device may be used to determine whether received additional physiological measurement data of a person in the sub-group satisfies the second criteria. In the event that the additional physiological measurement data satisfies the second criteria, an associate intervention may be taken. As described above, interventions can include, for example, at a first level, informing the concerned person or representative and informing of the actual health-related concern, at a second level of intervention, informing the concerned person or representative of an action indicated by the actual health-related concern. In some embodiments the actual person may be contacted, or in other situations, a care giver, emergency contact, relative or other concerned individual may be contacted.

In another embodiment, a method for managing health care made available to a group of people is provided in which initial physiologic measurement data related to a potential health-related concern from each of a plurality of people in the group is received. Additional physiological measurement data is also received that is related to each person in a sub-group of the plurality of people whose related initial physiological measurement data satisfies at least one first criterion obtained using a portable device provided to each person in the sub-group. For each person in the sub-group whose additional physiological measurement data obtained by a portable device satisfies at least one second criterion, a level of intervention associated with the satisfied at least one second criterion may be performed. For example, in a blood pressure sub-group that may be populated by individuals having blood pressure above a certain criterion, those individuals who have an additional or further blood pressure measurement that exceeds a second criterion may have an intervention which can be, for example, a reminder to take medication, a telephone call to the person, a 911 call, or other intervention.

In another embodiment, a method for managing health care made available to a group of people is provided in which initial physiologic measurement data related to a potential health-related concern from each of a plurality of people in the group may be received. With the aid of a computing device, persons may be identified for a sub-group, each person in a sub-group of the plurality of people whose related initial physiological measurement data satisfies at least one first criterion. Each person in the sub-group may be provided a portable device capable of providing additional physiological measurement data related to the potential health concern. Additional physiological measurement data may be received from each person in the sub-group that is obtained using the portable device provided to each person in the sub-group. A computing device may be used to identify each person in the sub-group having received additional physiological measurement data that satisfies at least one second criterion. For those persons having such a physiological measurement, an intervention associated with the at least one second criterion may be performed.

In another embodiment, a method for managing health care may be provided in which initial physiological measurement data of persons related to a health concern may be received. A monitoring device may be provided to a person who has been prescribed a regimen relating to the health concern, the monitoring device providing physiologic measurement data related to the health concern. One example of a prescribed regimen can be, for example, periodic or on-time administration of a medication. Other prescribed regimens can include, for example, appropriate diet, exercise, medical treatments, sleep or other regimen. Data obtained by the at least one monitoring device may be received and based on the initial physiological measurement data and the physiological measurement data received from the monitoring device, a determination may be made to intervene to determine compliance with or the effectiveness of the regimen.

In another embodiment, a method for managing health care is provided in which at least one monitoring device is provided to a person having a health concern possibly affected by the occurrence of a condition external to the person, the monitoring device providing physiologic measurement data related to the health concern. One example of a condition external to a person is an environmental condition, such as pollution, smog levels or a high or low temperature which may have a deleterious effect on lung capacity, blood pressure, or other health condition, or which may cause a health concern, such as weight, diabetes, blood pressure, or other concern, to be affected. Data obtained by the at least one monitoring device may be received. In general the data relates to a person's physiologic measurement data which may relate to the health concern. Occurrence of the condition may be monitored, e.g., by monitoring weather or pollution information. A determination to perform an intervention with the person related to the health concern may be made based on the monitoring and the received physiological data.

BRIEF DESCRIPTION OF THE DRAWINGS

The invention is illustrated in the figures of the accompanying drawings which are meant to be exemplary and not limiting, in which like references are intended to refer to like or corresponding parts, and in which:

FIGS. 2-12 are graphic user interface screens for authorized persons to access information obtained with the monitoring devices and to communicate with the monitoring devices according to one embodiment of the invention.

DETAILED DESCRIPTION

Figure 1:
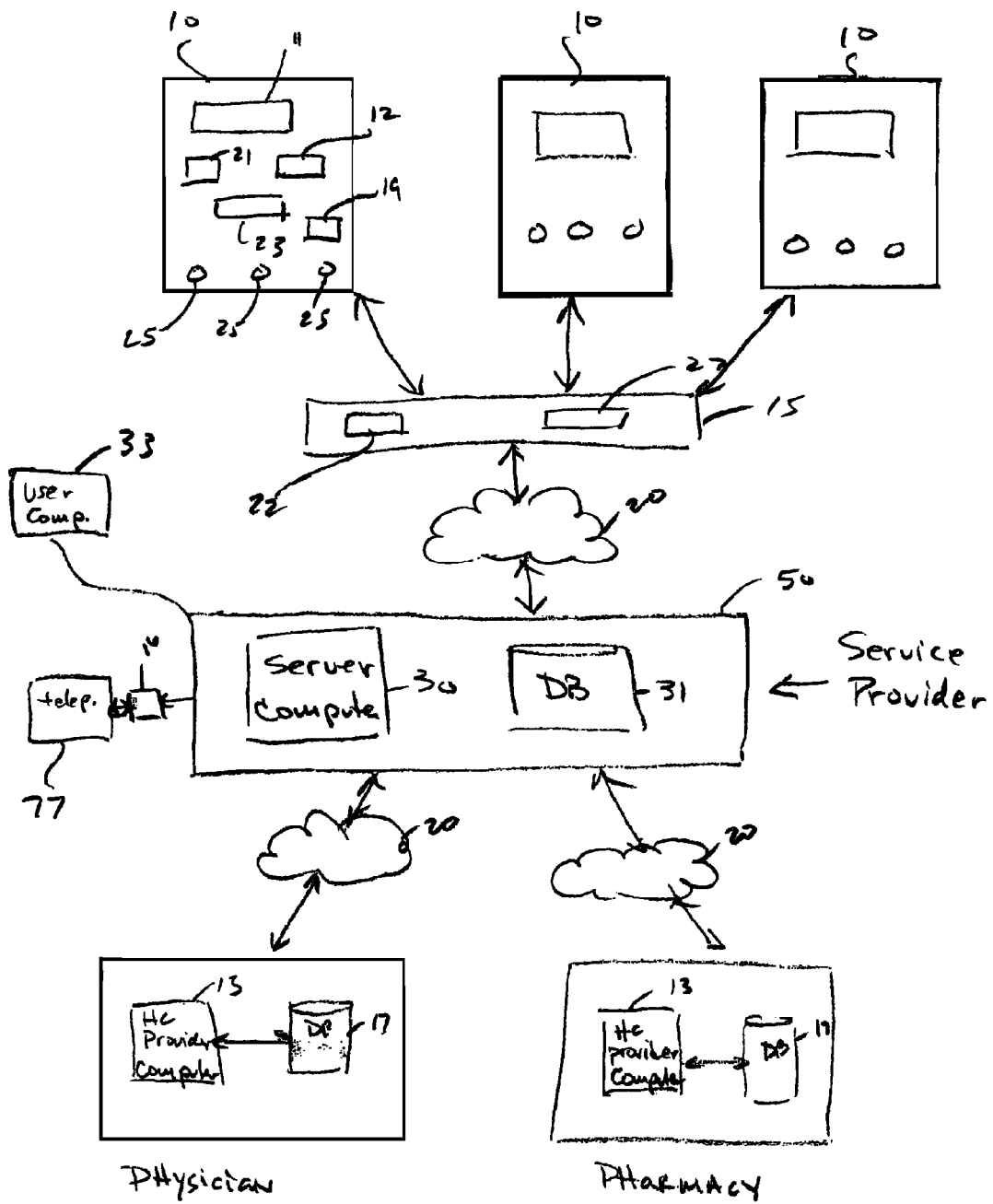
FIG. 1 is a block diagram of a system according to one embodiment of the invention.

Referring to FIG. 1, in one embodiment of the invention, a medical monitoring system is provided that includes at least one computer 30 communicatively coupled to one or more monitoring devices 10, via a transmission device or hub 15, over a communications network 20. Computer 30 is generally one or more server or host computers with access to one or more databases 31 that provide the remote functionality described herein. In one embodiment, computer 30 is not located locally with respect to monitoring devices 10 and may thus be referred to as a remote computer. In one embodiment, the monitoring system includes at least one computer 30 communicatively coupled to a plurality of different types of monitoring devices 10, through the transmission device or hub 15 or otherwise.

A monitoring device 10 is generally a data acquisition device for obtaining and/or monitoring subjects for physiologic or other information. (The terms "subject," "member," "user," "individual" are used in a broad sense and may be used interchangeably unless the context indicates otherwise.) The monitoring device 10 preferably includes, e.g., incorporated into the device, at least one sensor 12 for measuring or otherwise sensing directly at least one physiologic parameter of a subject. Various types of sensors may be included in the monitoring devices 10, including, but not limited to, sensors that are used for determining glucose level, weight, blood pressure, body temperature, heart rate, EKG, EEG, substance presence or levels, therapeutic effect, efficacy, compliance, etc. The monitoring devices 10 may therefore be multi-purpose devices, e.g., having a plurality of sensors for measuring different types of physiologic parameters, or different types of devices 10 for measuring different types of physiological parameters, such as a weight scale to obtain a user's weight, a blood pressure cuff to obtain a user's blood pressure, a glucose monitor to obtain a user's blood glucose level, etc., or any combinations thereof, such as a combined glucose and blood pressure measurement device. In certain embodiments, the monitoring device 10 is portable and designed to be wearable by a subject or easily carried.

In one embodiment, the monitoring device 10 includes one or more of the following: an electronic controller 23, an electronic memory 21, a user interface 25 for a user to input information therein, such as buttons or keypad, an output device, such as a display device 11, e.g., a graphic, non-backlighted monochrome liquid crystal display, a communications unit 19, and a power source (not shown), such as batteries. The device 10 preferably includes a clock and/or a calendar or other means for associating a time and/or date with a physiologic measurement. The memory 21 generally provides a means for storing information collected therewith or received from the remote computer 30, such as a plurality of measurements, statistical data derived from the measurements, e.g., in chart form or otherwise, user information, e.g., a user identification number, device information, e.g., a serial number, and time and date information. Some or all of the user information may be stored in the monitoring device 10 memory, for example, for later review. The monitoring device 10 is preferably powered by standard batteries or chargeable using a power charger, and may include a battery meter on the display device indicating the power remaining in the monitoring device 10.

In one embodiment of the invention, a medical monitoring device 10 is provided, which includes an electronic controller 23, a display device 11, an electronic memory 21, and one or more sensors 12 for measuring at least one physiologic parameter of a subject. The sensor may also detect consumable usage and/or test or otherwise determine at least one physiological parameter of a subject using the consumable. In this respect, the invention beneficially allows an authorized party to determine compliance based on actual usage of a consumable as opposed to indirect or assumed usage based on reporting acts from a subject. For example, actual usage may be assured with a device that determines both usage and blood glucose from a blood glucose sensor.

The monitoring device 10 may also include a communication unit, e.g., incorporated into the device, which communicates information measured or otherwise obtained therewith or any other information stored in the computer memory 21, such as responses to messages, to a transmission device 15. In preferred embodiments, the monitoring device 10 communicates with the transmission device 15 using suitable wireless technology, such as an RF carrier, although other wireless, or wired, communications may be used. In this instance, the device 10 includes therein an appropriate transmitter and/or a receiver for communicating with the transmission device 15.

The transmission device 15 generally acts as a hub or base for one or a plurality of monitoring devices 10, e.g., a plurality of different types of devices, which communicates information received from the monitoring devices 10 to the server computer 30. In this respect, the transmission device 15 generally includes a communication unit 27 for communicating with the monitoring devices 10 and a communication unit 29 for communicating with the server computer 30. For example, the transmission device 15 may include a transmitter and/or a receiver for communicating wirelessly with one or more monitoring devices 10 and a modem and/or a jack, connector, or other port for connecting to the server computer 30 over a network 20, such as a cellular telephone network, the public telephone network, the Internet, or any other network. The plurality of different types of monitoring devices 10 preferably communicate with the transmission using a common protocol thereby allowing a single transmission device 15 to be used as a hub for a number of different types of devices 10.

In one embodiment, the transmission device 15 communicates automatically with the monitoring devices 10 and/or with the server computer 30 without any direct prompting from a user. For example, with regard to a monitoring device 10 for monitoring a subject's blood pressure, the monitoring device 10 may automatically signal the transmission device 15 when a physiologic measurement has been taken and may automatically communicate necessary information, including the measurement, to the transmission device 15. The monitoring device 10 may also signal the transmission device 15 prior to taking a measurement, e.g., when the device is turned on. In this respect, the transmission device 15 may attempt to connect with the server computer 30 while the measurement is being taken to shorten any response time from the server computer 30. This aspect of the invention beneficially enhances the user's experience with regard to the real time responsiveness from the system. The monitoring device 10 may also store information therein for later communication, e.g., in the event the monitoring device is not able to communicate with the transmission device 15, and attempt to establish communication with the transmission device 15, as discussed below. The transmission device 15 may then automatically establish communications with the server computer 30 and communicate the information received thereto. In this respect, the transmission device 15 does not require a display, however, a signal indicator may be provided, such as an LED or LEDs, which, e.g., flashes to indicate communication is taking place and/or indicate status of the communication. Where transmission device 15 includes a cell phone, which typically includes a display, such display need not be part of the subject experience in the process of communicating between a transmission device and a remote computer or using the monitoring device or sensors.

The transmission device 15 is preferably a portable device, which can be easily transported and can establish a communication connection wherever it is located. In other embodiments of the invention, transmission device 15 is fixed in one location, for example, within a subject's home. As noted above, the transmission device 15 may also be configured to operate with a plurality of monitoring devices 10, as shown in FIG. 1, whether of different types or otherwise. In this instance, the transmission device 15 may be configured to recognize or otherwise identify each of the plurality of monitoring devices 10. This may be accomplished, for instance, with a unique device identifier that is communicated to the transmission device 15 with the physiologic or other information. In other embodiments, more than one subject may use the same monitoring device 10. In this instance, the monitoring device 10 and/or the transmission device 15 may be configured to associate a particular patient's or subject's information with the appropriate person. This may be accomplished by prompting the user of the device 10 to identify himself or herself, in which instance, a unique subject identifier may be communicated to the transmission device 15 with the physiologic information. As noted above, the monitoring devices 10 may also include a clock for associating measurements taken therewith a time and date. In this instance, time and date information is communicated to the transmission device 15 with the physiologic information. In general, a monitoring device 10 may be provided to a person or an individual or a group of individuals as part of a treatment regimen to monitor a physiologic condition.

If communications with the transmission device 15 cannot be established immediately, e.g., soon after the physiologic measurement has been taken, the monitoring device 10 may attempt to establish communications at a later time. In one embodiment, the monitoring device 10 may attempt several times successively soon after the failed attempt. If communications cannot still be achieved, the monitoring device 10 may store the information and try to send the information at a later time, e.g., in 5, 10, 15, 20, etc. minute intervals.

The transmission device 15 generally communicates the information obtained from the monitoring devices 10 to a server computer 30 via network 20. The network 20 may be any network or a plurality of networks suitable for communicating information from the transmission device 15 to a remote computer 30, such as a cellular telephone network, or any other wireless network, the public telephone system, the Internet, a local area network (LAN), a wide area network (WAN), etc. The manner in which the transmission device 15 communicates to the server computer 30 will depend on the resources available. For example, when available, the transmission device 15 may be coupled to communicate via a cell phone, which provides for maximum flexibility with respect to monitoring subjects away from a particular location, e.g., the subject's residence. Similarly, when available, the transmission device 15 may communicate via the public telephone network or over the Internet. In one embodiment, the transmission device includes a plurality of different types of communications units 29, such as a modem, a USB port, a serial or parallel port, etc.

Communication of patient or subject information is preferably secure and/or encrypted. For example, patient information can be sent as a single UDP datagram and error checking can be provided (e.g., checksums, encryption, etc.).

In one embodiment of the invention, at least once, periodically, or each time the monitoring device 10 communicates with the transmission unit 15 and the computer 30 via network 20, date and time on the monitoring device 10 and/or the transmission unit 15 is synchronized with the date and time of the computer 30.

In one embodiment, the server computer 30 includes therein software, hardware, or a combination thereof, which establishes or at least attempts to establish communication with the user of the monitoring device 10 based on the information received therefrom. The computer 30, for instance, may initiate communication with the user based on physiologic measurements communicated thereto from the monitoring device 10. For example, the server computer 30 may compare incoming data with thresholds, e.g., established based on general standards or for the particular user, and initiate communication with the user when the incoming data exceeds the criterion or other threshold. For instance, if the system determines that the user's weight, blood glucose level, blood pressure, etc., or any statistical derivation thereof, exceeds a criteria, level or threshold for such measurements, the system may attempt to initiate communication with the particular measure accordingly. For example, if the user's blood pressure appears elevated based on a threshold set for the particular user or for a group of users, the computer 30 may initiate communication with the user to query the user regarding activities and symptoms that may be associated with the elevated reading. Thresholds may be established for a number of other criteria for establishing communication with the user of the device 10. For example, the time between measurements or non-measurement for a period of time may trigger communication.

In some embodiments, a plurality of interventions may be associated with each of a plurality of criteria or threshold. For example, in a blood pressure treatment regimen or a blood pressure group, different blood pressure levels may be established as a criterion, each of which may have an associate intervention. For example, for a somewhat elevated blood pressure measurement, an intervention may be a message sent to the monitoring device 10, which may be a free text message, include a query about medication consumption, or other message. For a slightly higher blood pressure measurement, an intervention may be a telephone call to the individual, a care giver, emergency contact, or other individual. For a dangerously high blood pressure measurement, other emergency intervention may be taken.

Various or a plurality of various types of communications may be initiated, including messaging back to the medical device 10, e-mail messaging, facsimile messaging, voice messaging, etc. In one embodiment, the computer 30 is communicatively coupled to a public telephone network 16 that provides access to the user with user telephonic equipment 77. Messages can include free text which may relate specifically to a particular user, data obtained by the monitoring device 10 or other received data. Free text may include, for example, text that is written, generated, created or otherwise provided by a care coordinator, medical provider, concerned individual, or other person. The free text can include user-specific data and the free text message may be created in response to or relate to a user's physiologic measurement. The free text message may also include portions of predefined or canned text or other automatic messaging data.

In one embodiment of the invention, some or all of the communications between the various devices of the monitoring system are performed in real-time, when possible. For instance, information from the monitoring devices 10 may be communicated automatically to the transmission device 15 once physiologic or other information is obtained with the device 10, which may subsequently be communicated automatically to the server computer 30. The server computer 30 may monitor incoming information and establish or attempt to establish communication with the user once the information is received. In this respect, the monitoring system is capable of real-time monitoring and real-time responses to the monitoring data.

The type of messaging and the form of notification may vary based on the type of data received. For example, the messaging may be free text, words of encouragement for a user participating in a weight management program, statistical information based on the information received, prompts for additional information, prompts or directions to contact a person monitoring a user or a health care provider, etc.

In addition to automated messaging, e.g., automatic messaging based on information received, the system may further provide access to the information received and/or messaging capability to authorized users, such as users of the monitoring device 10, health care providers and professionals, partners, caregivers, family members, and any other interested party. In this instance, the server computer 30 may be communicatively coupled to a user computer 33, such as a personal computer, personal data assistant (PDA), cell phone, or any other communicatively enabled device, capable of displaying at least one graphic user interface for accessing the stored information, such as the interface screens depicted in FIGS. 2-12.

In one embodiment, the devices of the present invention and the information therefrom is used and/or compared with information obtained in a manner that is other than with self-monitoring, e.g., by a professional at a physician's office, hospital, pharmacy, laboratory, insurance agency, etc. In this respect, the monitoring system of the present invention includes or is otherwise communicatively coupled to a healthcare provider computer 13 that is associated with a database 17. The database 17 generally includes therein information regarding an individual being monitored obtained by, e.g., a healthcare provider during an office visit or in any other office setting. The database 17 may include any type of information relevant to the healthcare provider based on the particular type of service provided therefrom, such as physiologic measurements, laboratory or other test results, prescribed medications and dosage, refill information, etc. This information may be compared and reconciled with information obtained with the medical monitoring device, e.g., for accuracy or to identify any anomalies in the data. One example, of such reconciliation may occur when using an electronic prescribing tool in a doctor's or other medical or healthcare provider's office to electronically prescribe a patient's medication. Data entered in the electronic prescription may be automatically populated in the database 17 in the patient's medication record so that it may be compared and reconciled with the information obtained with the medical monitoring device 10. This way, the patient can be tracked for further diagnoses and progress, e.g., by comparing additional physiologic monitoring.

As discussed herein, a monitoring device or a plurality of monitoring devices 10 and a transmission device 15 can be located within a household to serve one or more users therein. The term household is used herein in a broad sense to include any location in which a monitoring device 10 and transmission device 15 may be located, and can include a hospital, institution, or other location. The households are connected to remote computer 30 via a network 20, described herein, which includes for example, a cellular telephone network, the public telephone system, the Internet, etc., or any other network. The computer 30 generally includes a processor, memory storage, and other common computer components suitable to execute the systems and methods described herein. The computer 30 will typically include or access a database 31 to store a monitored subject's information, as well as other information. The database is preferably a relational database. The database may generally include various types of information regarding the particular user that are relevant to the physiologic parameter being monitored, such as the user's contact information, physician(s) and their contact information, emergency contacts, medications, allergies, medical history, clinical evaluations, family histories, hospitalizations, medical visits, physiologic measurements, e.g., glucose, weight, blood pressure, etc., thresholds, goals, passwords or identification numbers, unique device identifiers e.g., serial number, etc. Some or all of information may also be maintained by a healthcare provider that obtains the information in a manner other than through self-monitoring, such as in database 17.

Computer 30 may communicate patient information or other information to service providers 50 and one or more recipients via network 40. Incidentally, one or more of the recipients may be a healthcare provider that maintains the database 17. For example, a physician may maintain a database of patients under his or her care, and may also have access to the patient information obtained with the monitoring device 10. The network 40 may be a cellular telephone network, the public telephone system, the Internet, etc., or any other network. Service providers 50 may be a doctor, hospital, medical provider, emergency medical services, or another service provider who may provide a service to a subject user based on patient or subject information, such as the information entered into or measured with the monitoring device 10. A recipient may be a family member, interested individual, or any other person who may wish to receive the monitored subject's information.

As noted above, the computer 30, service provider 50 and recipient may also communicate with the monitoring device 10 via the network 40, computer 30, network 20, and transmission unit 15, for example to supply information or questions in response to received patient information. An "envelope" icon or other message indicator, may appear on the monitoring device 10 display, or an audible message indicator alert may sound when such information is received from a service provider 50, a recipient or the computer 30. A message from the computer 30, service provider 50 and a recipient may require an acknowledgement from the user, for example, before a user can take a measurement or use the monitoring device 10, the user will be required to read a message and respond to it or otherwise acknowledge the message. The response or acknowledgement entered into the monitoring device 10 is communicated over the network 20 to the computer 30, service provider 50 or a recipient.

When a user first obtains a monitoring device 10, the user, in one embodiment, must register the monitoring device 10. For example, a user may enter an access code into the monitoring device 10 to "unlock" the monitoring device 10 to allow it to register with the system. Informed consent information, such as system terms and conditions, may also be displayed to a user and acknowledgement or acceptance required prior to initiating a monitoring device 10. In a first communication between the monitoring device 10, transmission unit 15 and computer 30, a connection may be established through a toll free number to register the user with the system and to download a local dial in number for future use. The access code may be a unique access code that may be stored with the device 10 to identify the particular device and/or the user, or some other unique identified, such as a serial number, may be stored with the device to identify the device, the user, or a combination thereof. In one embodiment, registration is initiated with the user taking the first measurement with the monitoring device 10. The first measurement may be communicated to the computer 30 with the registration information, or at some other time, such as on a subsequent communication session with the computer 30. In this respect, the subsequent communication will include a plurality of physiologic measurements.

After a user has registered or otherwise logged into the system using the monitoring device 10, a menu may be displayed on the display listing the primary information associated with the daily operations of the monitoring device 10, which depicts a display for a blood pressure monitor. The first menu may include a readings selection menu item for accessing physiologic information obtained with the device 10, a messages selection menu item for accessing messages communicated to the device 10, and an options selection menu item for specifying device options. Device 10 may also display button identifiers that identify the function of the buttons of the device, e.g., a scroll identifier, a select identified, etc. A user may select a menu item to go to a next screen that is displayed in response to the selection.

Upon selection of the readings menu item, the device may display a measurements screen that includes measurements obtained with the device 10. Measurements may be shown on the monitoring device 10 display in more than one way, such as numeric data or graphical data, or a combination thereof. Measurements are preferably shown in the order of the measurement, e.g., by time, day, week, month, etc. The device preferably provides scroll functionality to display readings for other days. The graphical representations of the measurements may be determined locally, e.g., on the monitoring device, or remotely, e.g., by the server computer 30, in which instance, the server computer may communicate coordinate data, as well as other graphical data, for displaying the graphical image of the measured data on the display of the monitoring device 10.

Upon selection of the messages menu item, an appropriate messaging screen is displayed. The messaging screen may provide a list of opened and unopened messages, which may be selected by the user for viewing. Upon selection, the contents of the selected messages are displayed. As noted above, messaging may vary. The messaging may be a prompt for information, such as a compliance query, which shows a message from, e.g., computer 30, a service provider 50, or a recipient, inquiring whether the user has taken medication. Similarly, the messages may inquire regarding use of the device, which may serve as a gentle reminder for the user to use the device 10 more often. Other free text messages relating to received data may also be sent to the device 10.

The monitoring device 10 options can be changed by selecting an option selection on the display menu, which may provide access for changing configurable features, such as alerts, beeper, signal, connection, or transmission features. Connection settings generally permit a user to set connection preferences, such as dial up number, dialing pattern, line access, etc. Alternatively, or in addition, the transmission device 15 automatically determines the type of connection being used. Transmission settings also allow a user to set transmission, e.g., enable or disable, for example when a user is in a hospital and transmission must be turned off.

To initiate a measurement, a user may select a start button on the device. Selecting the start button can cause a graphical representation that instructs the user of the proper placement and/or use of the monitoring device 10 screen. With regard to a blood pressure cuff, the correct placement of the monitoring device 10 is depicted to assist the user in obtaining a correct blood pressure measurement.

When a user is ready to take the measurement, the user may so indicate through an input to the monitoring device 10. When the measurement is completed, the reading will generally be displayed on the screen of monitoring device 10 and stored to memory at least temporarily with the time and date the measurement was taken. If there was an error in the measurement, an error message may be displayed on the screen, and the user may be prompted to repeat the measurement.

In at least one embodiment of the invention, the subject's information is communicated from the monitoring device 10 to the computer 30 via network 20 at about the time the measurement is taken. The monitoring device 10 screen can include indications that the user's information is being transmitted, such as a transmission or connection icon. When the computer 30 has been reached, confirmation that the information has been received by the computer 30 may also be indicated by the monitoring device, e.g., with a display on the monitoring device 10 screen, or an audible signal. If computer 30 cannot be reached, an indication of the failed communication will be indicated on the monitoring device screen.

The monitoring device may include a plurality of input devices such as buttons and other devices that are used in conjunction with the display to provide the monitoring device 10 user interface. The monitoring device 10 may include several device drivers, such as a Timer Manager that maintains, e.g., a 10 millisecond, time base to provide system wide timing for the polling of keys or buttons, updating the display and other general purpose timing requirements, a Display Manager that provides a transparent interface to the LCD display, a Keypad Manager that debounces and posts keypad entries to the application software, an Eeprom Manager that provides an interface for non-volatile data storage, a communications Manager that provides access to/from the communication (RF) system, or other device drivers.

The Timer Manager generally uses a timer to generate an interrupt, e.g., every ten milliseconds. The timer manager maintains a timer for each of the following: Keypad Poll Timer, e.g., of 20 milliseconds, which when the time expires activates the keypad manager so that it can poll, debounce, and post any keys that have been pressed, a Beeper Timer, which allows a single-tone beeper to be activated with a variable duration On/Off time, and General Timers, which are used by the application to send callback messages to itself at defined intervals.

The Display Manager performs initialization of the monitoring device 10 display controller and accepts text strings (Null terminated character arrays) from the application for display on the monitoring device 10. The API calls may include:

InitDisplay( );
This initializes the display controller.
ClearDisplay( );
This clears the display of any data.
DisplayString(char*string, byte_t position, byte_t mode)
This displays a text string at the starting at the desired character position.

The modes are: Normal, Inverse, Underscore

The Keypad Manager may be invoked by the timer manager at a rate of 20 milliseconds. The manager maintains a state machine to debounce and process key presses. Multiples of the 20 millisecond rate are used to move a key or button through the state machine. The states of the state machine may include: New Key—Key initially pressed, Waiting For Debounce—Key is held, Debounced—Key was held for required time. When a key reaches the Debounced state, it is posted to the application.

The monitoring device 10 memory can be, for example a 25LC640, 64K bit Serial Electrically Erasable PROM [EE-PROM]. The memory is accessed via a Serial Peripheral Interface (SPI) compatible serial bus. The bus signals required may be a clock input (SCK) plus separate data in (SI) and data out (SO) lines. Access to the device may be controlled through a Chip Select (CS) input. Data stored in the Memory can include, for example: system database, multiple measurements, chart data, messages from system, user identification, serial number, time data for the measurements, etc.

The monitoring device 10 may include a built-in A/D converter that is used to measure the battery voltage. The state of the battery is displayed as an icon on the LCD. Three levels: High, medium and low may be represented using these icons. A measurement of the battery may be taken each time that the monitoring device 10 enters a main menu screen, or, for example at power up.

The transmission device 15 software may be a real time system that is designed as a combination of an interrupt communication system and a polled event handler. The communications sub-system handles RS232 communications (cell phone and modem) as well as radio frequency communications, Bluetooth or other communication means, with the blood pressure meter or any other device. The transmission device 15 carries out commands to connect via a network, such as the Internet, cellular telephone, public telephone, to computer 30, and acts as a conduit for communications between the computer 30 and the monitoring device 10.

In one embodiment, the transmission device 15 generally has a modem, such as CMX866 integrated modem chip. The CMX866 is a multi-standard modem for use in telephone based information and telemetry systems. Control of the transmission device 15 is via commands, such as AT commands over a 9600 bps serial interface. The on-chip μController interprets these AT commands and controls an internal DSP, which provides the modem and ancillary functions such as Ring Detection, Call Progress Detection, Hook Switch control and DTMF autodialing.

The transmission device 15 can also have a cellular telephone interface, such as a RS232 serial interface. Hardware flow control using RTS/CTS is implemented. The signal lines available are: Transmit, Receive, RTS (Request to Send), CTS (Clear to Send), and Ground.

The monitoring device 10 and the transmission device 15 (collectively a "client device") may communicate with the server computer 30 in a variety of ways. In one embodiment, the client device communicates with the computer using the protocol outlined in Appendix A. The data may be communicated between the devices in a variety of different ways. In one embodiment, the information is communicated to the server 30 in a datagram or packet that includes at least one actual measurement taken with the monitoring device 10, such as a blood pressure, weight, glucose measurement and the date and time the measurement was taken. Additional information for associating the measurements with a particular user may also communicated to the server 30, whether in the same datagram or otherwise, such as a unique user identification number, access code, etc., as well as information for identifying the particular type of device being used, such as the serial number, responses to messages, request datagrams, acknowledgement datagrams, etc. Request datagrams generally contain a query or request for action from the receiving device, such as a request to logon, logoff, accept physiologic measurements, download charts, messages, etc., from the monitoring device. Acknowledgement datagrams generally contain information that acknowledges a request or completion of a request. For example, an acknowledgement may be communicated from a monitoring device 10 to the computer 30 indicating receipt of a physiologic measurement, a message, etc. The acknowledgements may be used, e.g., to track which information items where communicated between devices, such as measurements, charts, messages, etc., to prevent inadvertent multiple transmission of the same information. The various types of requests and acknowledgements are outlined in Appendix B. Various types of information may also be sent to the monitoring device 10 from the computer 30, such as chart data, e.g., coordinates as well as other information for plotting a graphical representation of the measure data, messages (long and short form), request datagrams, acknowledgement datagrams, etc.

As discussed above, computer 30 may include one or more databases which store information of the type described herein, e.g., patient data, health and medical condition data of individual patients, health and medical condition data in general, and/or drug tests, clinical evaluations, data, etc. Computer 30 and/or other computers may access, analyze and process such data in connection with a specific health issue or condition, etc. Information from such a database and other databases may be provided, e.g., for research, analysis or other purposes stripped of user information that may be used to identify particular users, such as the user's name, address, identification number, etc. Where a monitoring device 10 includes an input device or another means for entering information is provided, patients may enter demographic information and other information that may be included, e.g., with other patient information for, e.g., analysis and research purposes. Patient information may also be used in connection with the provision by a remote computer and appropriate databases of targeted messages, e.g., health related news, alerts, advertising, etc. For example, where a monitoring device supplies blood pressure information, the data may be used to identify the patient associated with the monitoring device as a candidate for a hypertension drug, etc. Such a patient may be supplied with an alert of extreme high or low temperatures, or ozone content, e.g. based on a geographic position. A monitoring device that supplies respiratory information may be identified, for example, as a candidate for an alert of high ozone content, or high air pollution levels, etc. The above or another database may be provided for compliance information.

In this respect, the service provider 50 may provide a website or any graphical interface for accessing information, which will generally be referred to herein as a website, for access to such information and/or for messaging particular monitored users. The particular user's information is preferably made available based on specific user entitlement. For instance, a monitored user may be entitled only to information regarding the user's own monitoring, such as the user's own physiologic measurements, charts, messages, etc. Similarly, a physician, caregiver, family member, or other interested party will have access only to information particularly entitled to, such as the interested party's own patient(s), family member, etc. In this respect, the monitored user may be provided with an interface or some other means for providing access to his or her information for interested parties. Website users may also be provided with information regarding monitored users without authorization provided the information does not contain any personalized information. For instance, the website users may be provided with statistical data regarding other monitored users, such as average readings for other users with similar conditions, compliance, outcomes, etc. In these respects, website users may first be provided with a logon interface screen prompting the user for a user name and a password.

As noted, a variety of interested parties may be provided access to information based on specific entitlement. For instance, a healthcare provider may be provided access to information for the provider's own patients. The term healthcare provider generally includes any individual or entity that is interested in the patient's physiologic measurements, such as a physician, nurse, aid, personal trainer, etc. In this respect, after logging on, the healthcare provider will be provided with a list of menu items, e.g., collectively under a "My Ideal Life" heading, that provide authorized access to specific types of information, such as personal information regarding all of the provider's patients or subgroups thereof, information regarding the provider's patient's readings or subgroups thereof, e.g., reports, messages or action items (interactions) for the particular provider, an online calendar, etc., as shown in FIGS. 2-12.

The service provider 50, i.e., in this instance, the entity supplying the functionality of the computer 30 and database 31, may provide the interface to a healthcare provider for the provider to manage the health of a group of individuals. Various types of health problems may be managed in accordance with the present invention, such as high or low blood pressure, glucose levels, weight, etc. The individuals may be grouped based on a variety of criteria, such as health related issues, common physicians, common insurance, etc., or a combination thereof. For example, physiological measurement data of a group of individuals may be received and compared to an initial criterion established for a sub-group. The members or persons in the sub-group may be associated with a particular treatment regimen appropriate for their health condition and be provided a monitoring device. Several levels of physiological measurement criteria may be established which correspond to an appropriate intervention for the criteria. For example, in a diabetes sub-group having members that have a particular glucose level that satisfies an initial criteria, one or more criteria may be established for different glucose levels which may have an appropriate intervention.

In this embodiment, the monitoring system of the present invention is used to manage the health of a group of users belonging to a coordinated care group. In this instance the service provider 50 is preferably a separate and distinct entity from the healthcare provider, insofar as the service provider provides the backend functionality of the service provider system, collectively the computer 30, database 31, and the software associated therewith. In this respect, a group administrator may provide the monitoring devices to its members and monitor the member's health with the interface provided by the service provider. A secondary observer, e.g., other than an actual physician, such as a nurse practitioner, may monitor the members' health to help doctors control the members' health more efficiently. In one embodiment, the interface provides information and alerts as well as other functions for the nurse practitioner to act as a care-coordinator that facilitates coordination between the physician and the patient.

As noted above, the healthcare provider may maintain the group members' information in a database 17 associated with a healthcare provider computer 13. At least some of the members' information, such as the members' names, addresses, demographic information, physiologic measurements, etc., may at least initially be shared with the database 31 associated with the remote server computer 30. This may be accomplished to define the coordinated care group. Once the group has been defined, the group administer may provide the monitoring devices to the members of the group, which may then activate the monitoring devices 10 by registering the devices 10 with the service provider 50 as discussed above.

In one embodiment of the invention, individual members of the group are monitored in accordance with a patient monitoring program or treatment regimen. The patient monitoring program generally includes a protocol that serves as a schedule for individual users to take additional physiologic measurements. The protocol may be fixed for the duration of the monitoring period or may vary. In one embodiment, at least one individual is monitored in accordance with a multi phase monitoring program, which may include a first phase for screening individuals for coordinated care regarding a health related issue indicative of a physiologic parameter being monitored, e.g., using an initial criterion as a comparison against physiological measurements to determine whether an individual is appropriate for a coordinated care sub-group (Phase I), a second phase to achieve control of the health related issue (Phase II), a third phase for screening individuals to determine if the health related issue is being controlled (Phase III), and a fourth phase for determining whether the health related issue is being controlled over an extended period of time (Phase IV).

The various phases may be timed accordingly. For instance, the first phase may entail measurements for a period of 8 days or any other time necessary to determine if the individual is a candidate for coordinated care with regard to a health related issue, such as high blood pressure level or other initial criteria for a group in coordinated care. Qualification for coordinated care may be based on a variety of criteria, which includes at least one physiologic measurement exceeding an acceptable threshold. If the individual is a candidate for coordinated care, the individual may be monitored for a longer period of time, fixed or otherwise, or until control of the individual's health related issue is achieved. Control may generally be achieved with coordinated care based on the physiologic measurements taken with the monitoring device 10. That is, the care-coordinator may review the physiologic measurements and/or any alerts derived therefrom and act accordingly in a proactive manner to control the health issue. It is understood that control may be achieved in a variety of ways, such as by prescribing medications or changing dosage, scheduling follow-up visits with a physician, attending to non-compliance issues, etc. Once the time period for control has lapsed, e.g., 6 months, the third phase may be applied to determine if the health related issue is indeed under control and, if so, the fourth phase may be applied to ensure that the health related issue remains under control. The various phases may generally be repeated as necessary until the desired control is achieved. In one embodiment, coordinated care with regard to high blood pressure may be achieved with the program outlined in Appendix B.

Group membership may be dynamic and based on a member's current health status. For example, if a member's physiologic measurements falls below or is considered better than an acceptable criteria or threshold, the member may be removed from the group. In another example, if more than one physiologic measurement is obtained from the member, one measurement may indicate a relative improvement of a condition which no longer exceeds an intervention or treatment criteria, but second measurement may worsen and exceed another criteria for membership in a coordinated care group or sub-group. In such case, the member may be moved from a first group to a second group.

Figure 2:
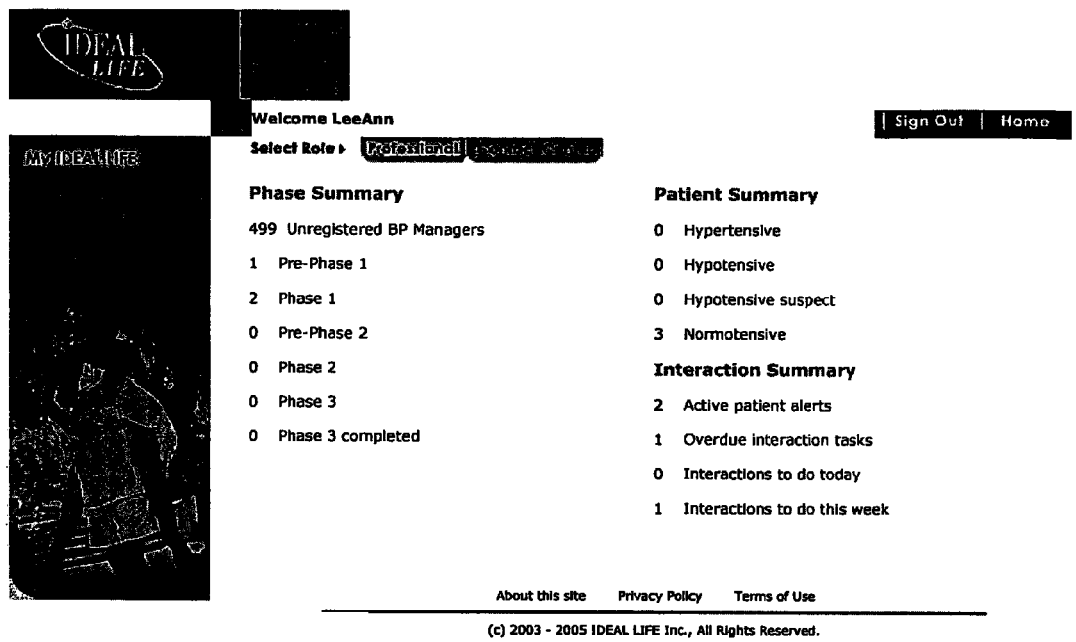
Figure 3:
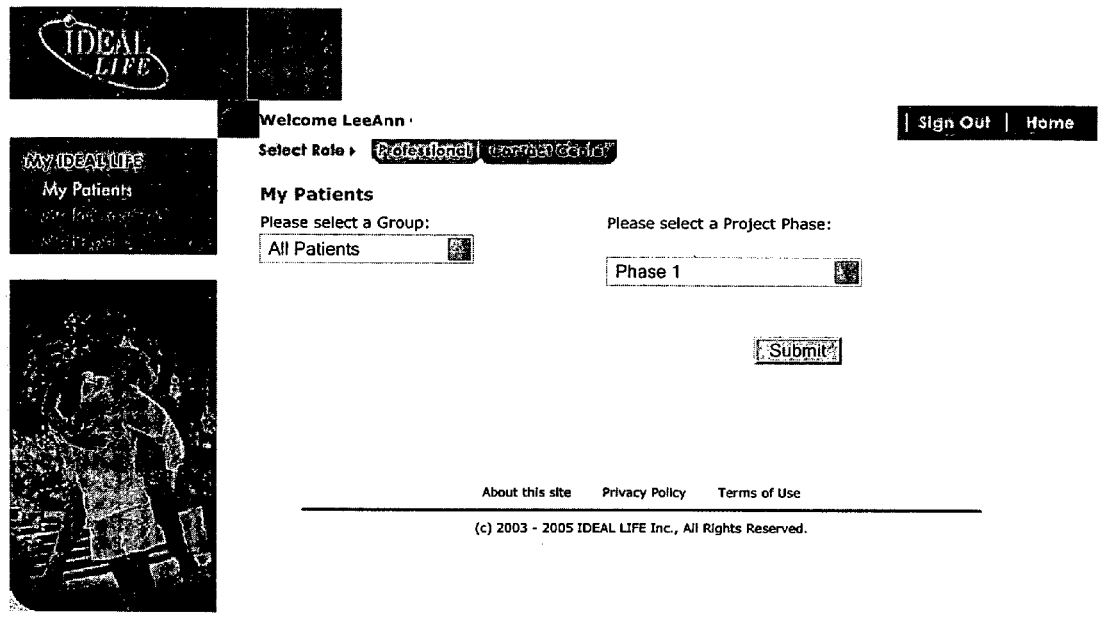

As noted above, the service provider 50 may provide a website that includes one or more graphic user interfaces for monitoring physiologic measurements for the members of the coordinated care group. The service provider 50 may provide a first interface screen or a dashboard that provides an overview with regard to the status of the coordinated care group in relation to the monitoring program, such as the interface screen shown in FIG. 2. Referring to FIG. 2, the first interface screen may include a program summary that indicates, for instance, how many of the members of the group have not registered their monitoring devices, and how many members of the group are in each particular stage of the program. The program stages are preferably selectable links that when selected cause to be displayed an interface screen that allows the care-coordinator to view information for the individuals included in the particular program stages, such as the interface screens shown in FIGS. 3 and 4.

The first interface screen may also include a patient summary that indicates how many members of the group fall within health related classifications, such as hypertensive, hypotensive, hypotensive suspect, and normotensive, and may include an interaction summary that indicates how many alerts and interactions are outstanding for the particular care-coordinator. Each of the classifications and the interactions preferably include selectable links that cause an appropriate interface to be displayed for viewing information regarding the individuals so classified and outstanding interactions, respectively.

Referring to FIG. 4, a patient interface screen may be provided that includes a list of the patients under the care of the particular care-coordinator. The interface screen preferably includes form elements, such as drop down lists, for the coordinator to define a subset of the coordinated care group. The subset of coordinated care group may be defined, for example, by health related classifications and/or program phase. The list preferably includes a color coordinated alert for each of the listed patients. The color displayed is generally based on the severity of the alert, which is generated based on physiologic measurements. Each of the listed patients may also have a selectable link associated therewith for displaying a patient summary interface screen or screens that includes additional information for the selected patient, as shown in FIGS. 5-12. The patient summary interface screen preferably includes a menu of selectable links for displaying additional information for the selected user, such as links for alerts, readings, office BP, medications, pharmacy, and reports.

Figure 5:
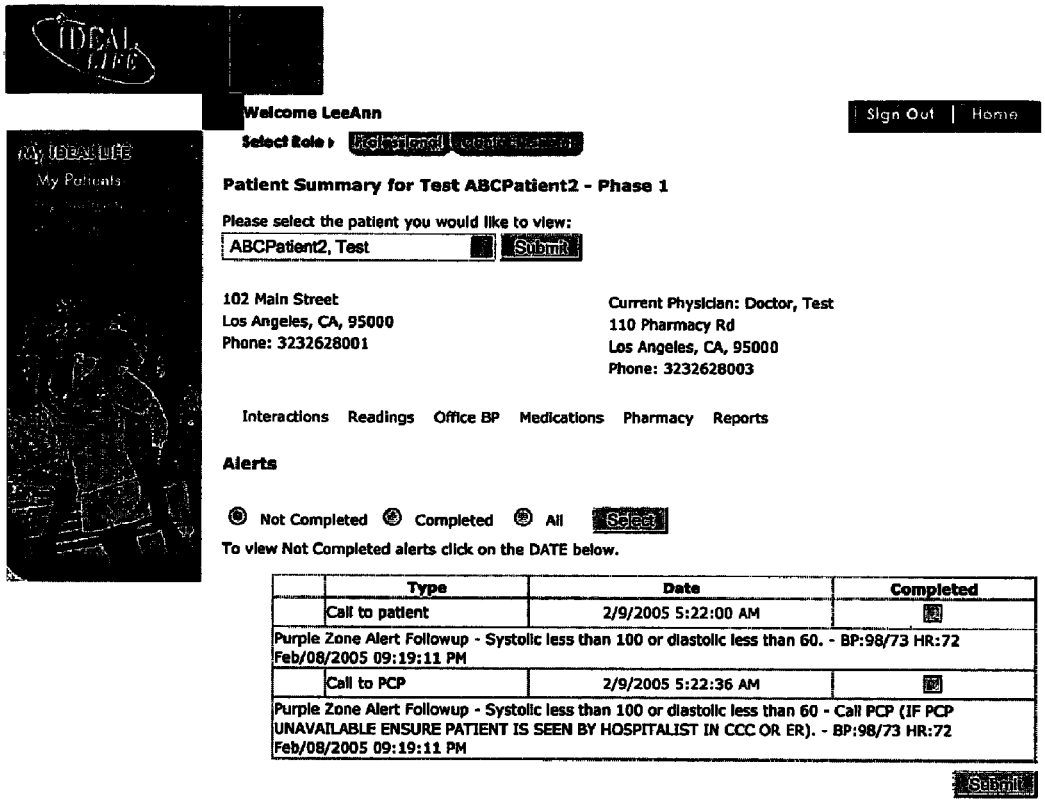

Referring to FIG. 5, in one embodiment of the invention, an alerts interface screen is displayed in response to the care-coordinator selecting the alerts menu item. The alerts interface screen generally provides a list of alerts for the particular care-coordinator. The interface screen may include a form element, such as a drop down list, for narrowing the alerts to a sub-set of all the alerts for the user, such as by particular patient, patient sub-groups, completed and not completed alerts, etc., or for broadening the alerts displayed. The individual alert items may include a form element, such as a check box, for the user to acknowledge receipt of the alert.

Referring to FIG. 6, in one embodiment of the invention, an interactions interface screen is displayed in response to the care-coordinator selecting the interactions menu item. The interactions interface screen generally provides a list of action items for the particular care-coordinator to follow up on. The action items may be triggered by the alerts or manually entered by another system user, such as a member of the group, a physician, a service provider, etc. The interactions interface screen may also include a form element, such as a drop down list, to narrow or expand the information displayed, and may include a selectable link that displays an interface screen for the care-coordinator to enter information regarding an existing interaction or create a new interaction for a particular member of the group, such as with the interface screens shown in FIGS. 7-8.

Referring to FIG. 9, in one embodiment of the invention, an Office BP interface screen is displayed in response to the care-coordinator selecting the Office BP menu item. The Office BP interface screen generally provides a list of physiologic measurements taken in an office setting. The interface screen may also include form elements for a user to enter such data therein and update the databases 17, 31 accordingly. In this respect, the information obtained by the particular healthcare providers may be entered directly into the service provider's system. Alternatively, or in addition, the information may be entered into the healthcare provider's system and later communicated to the service provider automatically. The service provider may also reconcile common data between the measurements taken or data entered with the monitoring device 10, and measurements taken or data entered in an office setting.

Figure 10A:
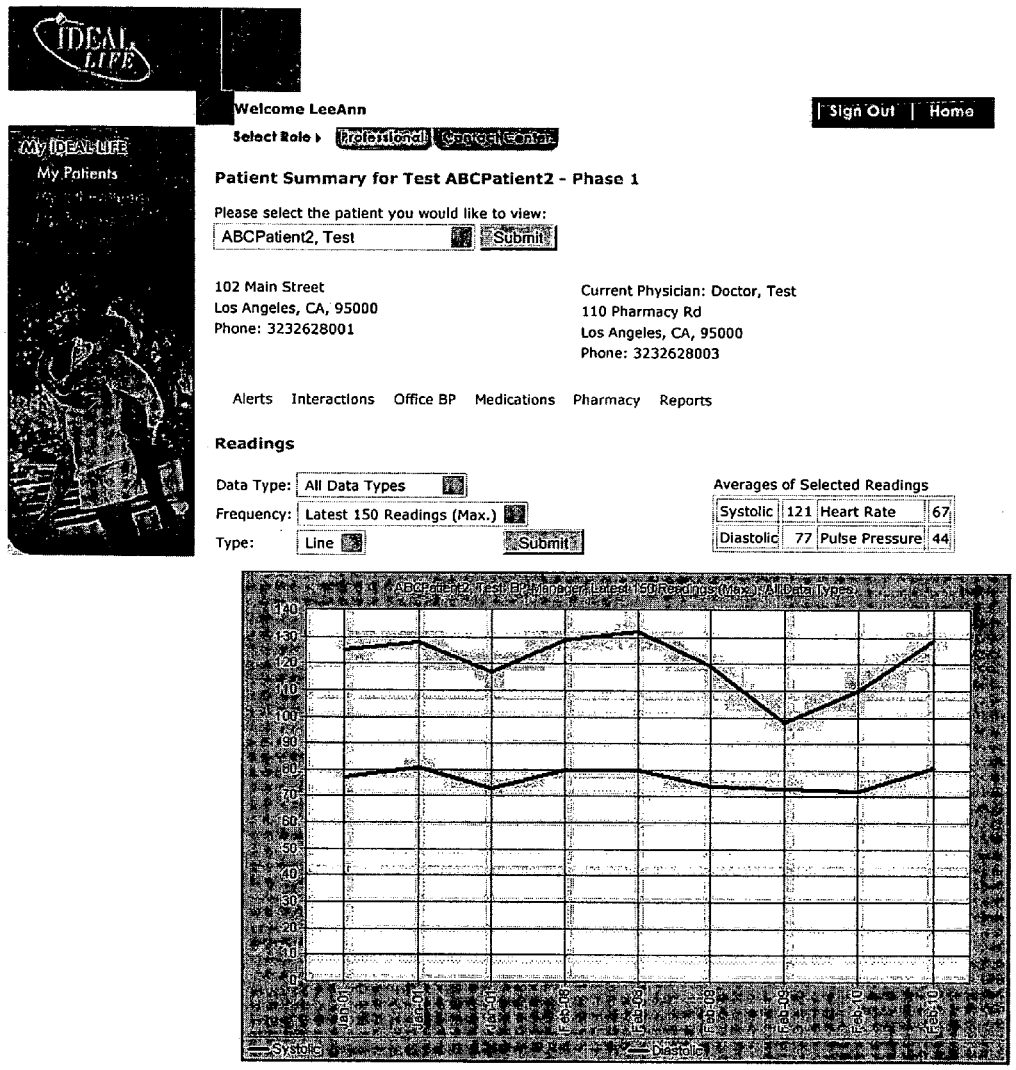

Referring to FIG. 10, in one embodiment of the invention, a readings interface screen is displayed in response to the care-coordinator selecting the readings menu item. The readings interface screen generally provides the physiologic measurements obtained using the monitoring device 10, which may be displayed in a graphic format or tabular format, or a combination thereof.

Figure 11:
Figure 12:
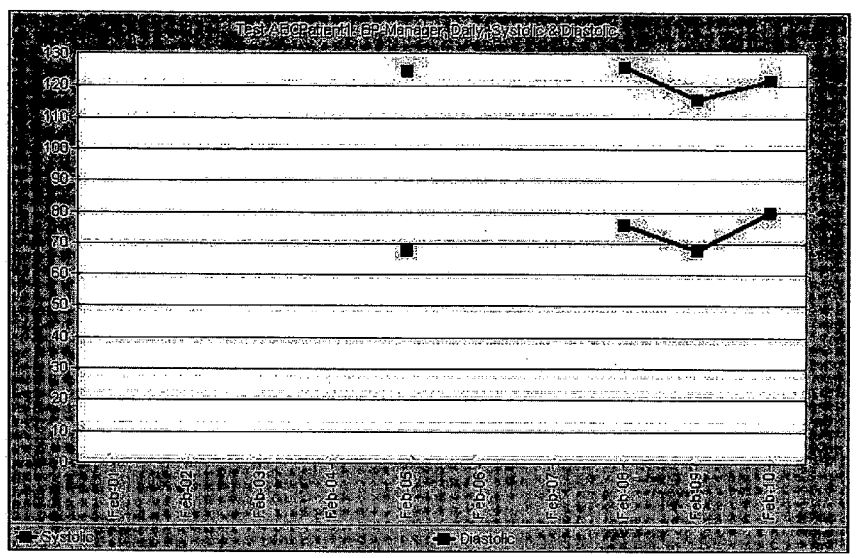
Figure 12:
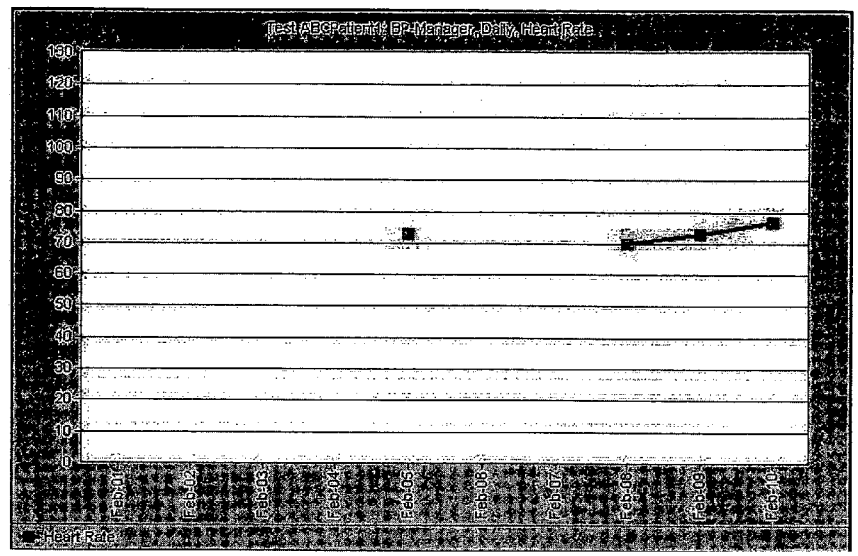

Referring to FIG. 11, in one embodiment of the invention, a medications interface screen is displayed in response to the care-coordinator selecting the medications menu item. The medications interface screen generally provides information regarding medications individual group members are taking or have taken. The information may similarly be entered manually directly into the service provider's system with form elements included in the interface screen, automatically from information maintained by a healthcare provider, such as a physician, pharmacist, etc., or a combination thereof. For example, an electronic prescribing tool may be used in a doctor's or other medical or healthcare provider's office to electronically prescribe a patient's medication. Data entered in the electronic prescription may be automatically populated in the database 17 in the patient's medication record and it may be compared and reconciled with the information obtained with the medical monitoring device 10. This way, the patient can be tracked for further diagnoses and progress, e.g., by comparing additional physiologic monitoring.

In one embodiment of the invention, a pharmacy interface screen is displayed in response to the care-coordinator selecting the pharmacy menu item. The pharmacy interface screen generally provides information related to prescriptions filled with a pharmacy. In this instance, the database 31 receives, preferably automatically, information regarding the prescriptions filled by the group member, such as the medication, the dosage, quantity, refills remaining, etc., from the pharmacy supplier. This information may be presented to the care-coordinator with the information provided with the medications interface screen, which is generally entered manually, allowing the care-coordinator to reconcile the data, e.g., with respect to changes to the prescription, and/or to determine compliance or more generally to get a better idea of whether or not the prescriptions are being filled or used properly. This information can then be reconciled with any changes in physiological readings. For example, with the information provided, the care-coordinator may determine whether the member of group is benefiting from changes to the prescription based on the readings obtained with the device 10. Similarly, the care-coordinator may associate non-responsive readings to non-compliance with changes to the member's prescription.

Referring to FIGS. 12*a*-*g*, in one embodiment of the invention, a reports interface screen is displayed in response to the care-coordinator selecting the reports menu item. The reports interface screen generally provides a report regarding the measurements obtained using the monitoring device 10 similar to the readings interface screen. The report interface screen preferably includes form elements for the coordinator to specify a date range for the report and the system will thereafter generate a report for the individual group member's health care provider. The report may be formatted for communication directly to the healthcare provider. For instance, the report may be formatted as a fax that includes a cover page with the recipients information automatically pre-populated in the form. Similarly, the report may be prepared as an email message with the to, cc, and subject items pre-populated. The data included in a report may also be stored in a raw format or other format in a database for data mining purposes, medical study, or other use.

The interface screens may also include form elements, such as a text box, for the care-coordinator to associate particular alerts and/or interactions with the data maintained by the healthcare provider. This may be accomplished, for instance, by specifying, with the form element, a unique identification number used by the healthcare provider to identify the records of particular group members. In one embodiment, the service provider 50 accesses the information maintained by the healthcare provider and provides an interface screen or window for the caregiver to view and preferably to search information maintained by the healthcare provider for information that may be required for inclusion into the care-coordinator's follow up notes that may be entered with the online website. Alternatively, the unique identifiers may automatically be associated with group members. In this respect, information maintained by the healthcare provider may automatically be accessible without the need for input by the care-coordinator.

In one embodiment of the invention, this association is used to provide the interface screens discussed above with a selectable link that provides direct access to the group member's information maintained by the health care provider. The selectable link may be associated with the group member's information in general or with particular items of information. For example, a link may be included in the interface screen that receives the group member's address or telephone number, or any other particular item of information maintained by the health care provider. The information may be displayed for use by the care-coordinator, e.g., in filling out form elements in the interface screens, or automatically used to populate the relevant form elements in the interface screens. The selectable link may also be associated with particular form elements. For example, when the care coordinator has to enter information for alerts, interactions, and even with other interface screens or pages, a selectable button, that may be shown as a blue question mark, may be displayed that when selected accesses the healthcare provider's local network and retrieves therefrom information that may then automatically be input into the relevant form elements of the website. This allows the care-coordinator to access a healthcare provider's internal network online and automatically fill in reference data into the website for later reconciliation (automatic or manual).

The backend functionality of the service provider's system, e.g., the computer 30, database 31, and the software associated therewith, is accomplished by processing the information obtained regarding the members of the coordinated care group, including physiologic measurements obtained with the monitoring devices 10 as well as information provided by healthcare providers, the care-coordinator, etc. The information may be processed continuously or in batch form. In one embodiment, the information is processed in accordance with the processing schedule in Appendix C.

In one aspect of the invention, a business model is provided for providing coordinated care. The business model involves activities of a plurality of parties, including the service provider that maintains and provides access to information obtained with monitoring devices, the healthcare provider that provides health related services to a plurality of individuals, and the plurality of individuals. The healthcare provider generally identifies at least one or preferably a group of individual's for coordinated care as described above. The service provider thereafter provides the monitoring devices to the healthcare provider for the group of individuals, either directly or through an administrator. The service provider may also provide all or some of the hardware and software needed to perform the monitoring, data acquisition, data storage, data processing, etc., to a group on a per member subscription basis. The monitoring devices may be purchased individually, leased, or included in a service subscription. Once a monitoring device is registered, the service provider will collect the information obtained with the monitoring device and make the information available to interested parties, including a care-coordinator. Data management and the functionality of the service provider's system as described above is generally sold on a subscription basis, e.g., per person per month. For example, an HMO may in this respect purchase monitoring devices for managing the blood pressure of a group of its members. The service provider will collect the data from registered monitoring devices and provide the backend functionality for the system for a monthly fee. The service may similarly be provided directly to the public. For example, the service provider may sell the devices and provide information regarding the information obtained, such as weight loss data, on a subscription basis.

A health manager may charge its members the cost of the per member subscription or device cost, and/or reduce membership or subscription fees by a projected savings to the group from identification and early intervention of members needing health care services. This model may also provide for the group underwriting the cost of devices used by members, so that the service provider avoids the need for a high capital investment for each group that the service provider serves. In this model, the service provider provides, maintains and operates a database (and associated communication protocols, data acquisition and access, etc.) which is used to service a plurality of groups. In one embodiment, the service provider may opt to provide the devices free or at low cost, and amortize the cost of the devices over the term of a contract with a group.

While the invention has been described and illustrated in connection with preferred embodiments, many variations and modifications as will be evident to those skilled in the art may be made without departing from the spirit and scope of the invention, and the invention is thus not limited to the precise details of methodology or construction set forth above as such variations and modifications are intended to be included within the scope of the invention.

APPENDIX A

1. Communications between a monitoring device and transmitting device (collectively "client device") and server computer.
    A. Client device Internet connection
        I. Client devices may communicate with servers using an Internet connection using a PPP (Point-to-Point Protocol) connection to the selected ISP (Internet Service Provider).
        II. The ISP will provide a national/international, e.g., toll-free, number for initial data access, and may also provide an extensive network of nationwide/international dial-up POPs (points of presence).
        III. The initial, e.g., toll-free number, as well as other information, such as a username, and password, may be loaded into all client devices for registration.
        IV. During registration, a local POP access number (or one that is as close as possible to the user's home address), username, and password may be sent to the client device, for further dial-up communications, unless it is remotely or locally reset.
    B. Communication protocol
        I. Communications sessions with the server computer may be initiated by the client device requesting either registration or logon to the server
        II. The client device may first resolve the name of the server using a DNS (Domain Name System) protocol, and use the IP address of the server for all further communications for the particular session
        III. The client device and server may communicate using the UDP (User Datagram Protocol) protocol, and a record may be sent as a single UDP datagram
        IV. Since UDP is a connectionless protocol with no guaranteed delivery, the server and the client applications may both be responsible for handshaking and monitoring communications timeouts
        V. A communication timeout may occur if there is no valid response from either the server or the client device for a period of, e.g., 20 seconds or if there is no valid transmission sent or received by either the client device or the server for a period of, e.g., 120 seconds. A valid response is a response which acknowledges a previous transmission and whose checksum is valid.
        VI. A communication timeout will terminate the session on both the client and the server, requiring the client device to initiate a new session before data can be transferred.
        VII. At a high level the sequence for datagram communications is as follows:
            a. Registration (a one time session to obtain a soft serial number, a user identification, etc.).
            b. Logon
            c. Send readings from client to server
            d. Send charts from server to client
            e. Send messages from server to client
            f. Send message responses from client to server
            g. Determine if a triggering event has occurred, if so initiate/conduct a messaging session
            h. Logoff
    C. Date and Time Synchronization
        I. The client device clock will be set by the server at the start of every session, i.e., registration or logon
        II. The server may synchronize with a time server on the internet to ensure accuracy
        III. The server computer may record, e.g., in the database, the home time zone for each client device when it is registered with the contact center, or more generally the service provider, based upon the user's home address
        IV. The server may convert and transmit all date and time information to the client device from "universal time", e.g., Greenwich Mean Time, to the user's home local time
        V. The server may convert and store all date and time information received from the client device from the user's home local time to "universal time"
    D. Language Preference
        I. The client device and the server may store the user's language preference
        II. The default language may be US English III. When the client device is first used or after a reset, the user may be asked to enter/confirm their language selection
IV. If the user specifies another language, the server may store the language preference and download the language preference to the client device during registration E. Registration
  I. Preferably, the client device may only be used once it has been successfully registered. On power-up, registration status is checked. If the device is unregistered, the user must enter, e.g., a five or six digit access code.
  II. The access code may be obtained by making a voice call to a contact center that provides a unique serial number necessary to initially register with the service. The contact center may link the access code to the serial number of the device in the database.
  III. The information collected by the contact center may include the full home address of the individual device user, including the postal code, so that a user's local time zone can be determined and stored on the server. The language preference for the user's client device should also be collected and stored by the contact center.
  IV. Client devices may not have their unique serial number in read only memory (ROM), instead the serial number may be downloaded from the server during the initial registration session. The serial number may be a unique integer, e.g., whose binary representation fits within 32 binary bits and is 10 decimal digits long, with a significant (non-zero) digit in the first position (i.e. decimal numbers from 1,000,000,000 to 4,294,967,295)
  V. To register the device, the customer may
    a. Make a voice call to the Contact Center or provide the information via the Contact Center web-site and obtain an access code
    b. Enter the access code on the device
    c. Connect the device to server, e.g., with the toll-free ISP access number
    d. The device will send a Registration Request datagram to the server
    e. Receive a Registration Datagram, with the serial number, local access number, username, password, language, date and local time, web address, ports and cellular phone configuration information from the server
    f. Send a Registration Acknowledgement record to the server
    g. If the Registration Status field is not equal to 0, the client device will reset itself to factory default settings and terminate the call, otherwise, the server will store the status of the device as Registered F. Logon and Logoff
  I. After successful registration, the client device will be required to logon to the server to start a communications session
  II. To logon, the client device may
    a. Connect to sever, e.g., using a local ISP access number
    b. Send a Logon Request record to the server
    c. Receive a Logon Data record, with the local time, etc.
    d. Send a Logon Acknowledgement record to the server
  III. The client device may initiate a normal logoff once all data to be sent from the device has been sent and acknowledged, and no data has been received and validated from the server for, e.g., 15 seconds. To logoff, the client device
    a. Sends a Logoff Request record to the server computer
    b. Receives a Logoff Acknowledgement record from the server computer G. Uploading blood pressure monitoring (BPM) Readings
  I. Once logged on the client device may start sending any readings that have not yet been successfully uploaded to the server
  II. One BPM Reading record may be sent in a single UDP datagram from the client device for each reading taken
  III. Each valid BPM Reading record sent to the server may be acknowledged by the server with a BPM Reading Acknowledged record.
  IV. If the BPM Reading record is already in the server database (i.e., the serial number, systolic, diastolic, heart rate, and converted bpm_reading_date all match an existing server database record) no duplicate record will be recorded in the server database, but the server may send a BPM Reading Acknowledgement record to the client device.
  V. The client device may modify its database when a BPM Reading Acknowledged record is received from the server to indicate that record should not be uploaded to the server again H. Downloading Charts
  I. The client device may send a chart request datagram to start the chart downloading process. This may be done anytime after a successful logon and readings transmission. The server acknowledges with a chart datagram, which includes the number of charts to be downloaded. The device then accepts one chart page datagram for each chart and acknowledges each one with a chart acknowledged datagram. The process ends when the number of charts expected is received and acknowledged
  II. By default the server may download all available (up to 10) chart types unless the user has specified otherwise, e.g., on the contact center's web site
  III. The server may generate a unique Chart ID for each chart that may be stored on the client device as well for unique identification
  IV. The chart types may include
    a. Systolic
    b. Diastolic
    c. Systolic & Diastolic
    d. Heart Rate
  V. The chart frequencies may be
    a. Latest
    b. Daily
    c. Weekly
    d. Monthly
  VI. To provide a graphical representation, e.g., bars, on the client device, the server may supply top left and bottom right absolute screen co-ordinates for each bar. The areas defined by the two extreme co-ordinates for a bar may be filled in black on the display.
  VII. The server may also transmit the values of the chart labels, such as values for Vertical Label 1 for the top label and Vertical Label 5 for the bottom Label. Similarly, Horizontal Label 1 may be transmitted for the left label and Horizontal Label 2 for the right label.

VIII. The server may also transmit the exact number of characters to fill each cell, including blanks for positioning properly within the cells.

I. Client Device Messages
   I. Users, Professionals, Caregivers, and Partners may use a form on the service provider web-site to enter and send messages to the client devices
   II. Messages may be available for these users, in a short format, long format, free text format, or other format. The short format may have fields for From, Subject, 5 lines of text and two button labels for user response, which will generally be displayed on a single screen of the client device. The long format message will have fields for From, Subject, and 5 lines of text for the first screen on the device, and the second screen will show the Subject and, e.g., six, multiple choice answers. For the long format message the button labels may be standardized on the device to permit moving to the next screen and selecting an answer.
   III. Once the user starts to review messages, all messages may be required to be reviewed/answered in order unless the escape button is pressed to exit the sequence.
   IV. Messages may be flagged as Alerts, and these may cause the device to beep when displayed to the device user until they are answered.
   V. The communications process for sending messages to the client device is . . . .
      a. Client sends MessageRequest datagram
      b. Server responds with Message datagram, which includes a field Number of Messages (left to send)
      c. Client responds with MessageAcknowledged datagram
      d. If message just acknowledged was a long format message, the server will send a MessageChoices datagram
      e. If a MessageChoices datagram was sent, the client will respond with a MessageChoicesAcknowledged datagram.
      f. Loop until all messages are received or a timeout occurs to end the session.
   VI. As the user reviews new messages on the device, the read receipt flag for that message is set in a corresponding MessageResponse record. As the user answers questions posed by the messages, the MessageResponse record stores the response. If a message has its alert flag set, the message may pop up on the device at specified intervals until the user creates an answer. All messages require a user response, even if it is only to indicate they have been read. Message responses may be sent in a later session than the one in which the messages were received or during the same session if so required.
   VII. The communications process for sending message responses to the server is:
      a. The client sends the next unsent MessageResponse datagram to the server.
      b. The server sends a MessageResponseAcknowledged datagram to the device. Once received, the device may delete the original message and its response.
      c. Loop until all MessageResponseAcknowledged datagrams have been received or a timeout occurs to end the session.

APPENDIX B

1. Screening Phases—patients screened for one week
   a. Patients monitor themselves 2 times per day, for 8 days (once in the morning between 6-10 AM and once in the evening between 6-10 PM)
   b. Calculation may be based on minimum of 10 readings, and days 2-8 (day 1 should not be included in the calculation of overall MEAN home BP)
      i. If miss a measurement, or miss a day, it will not affect the calculation, all numbers should be included regardless of time
      ii. If there is a need to go back later to verify times, some readings can be looked at twice for inclusion as all are time and date stamped
2. After screening
   a. Patients under drug therapy with office blood pressure ("BP") readings equal to or greater than 140/90 mmHg
      i. If the MEAN home BP is under 135/85 mmHg (<130/80 mmHg for diabetics and kidney disease), patients monitor themselves once every 2 months for 8 days (similar to first week screening method) until the end of the program, and followed up by the nurse once a month. In patients with the low normal range blood pressure (SYS BP less than 120 mmHg), treatment may be reduced or discontinued if there is concern about adverse affects related to hypotension (dizzy or light headed; ex. Pre-syncope). If drug therapy is reduced, patients may be enrolled in the full monitoring program.
      ii. If the MEAN home BP is equal to or greater than 135/85 mmHg (≧130/80 mmHg for diabetics and kidney disease): Hypertension is confirmed and the patient is enrolled into the full monitoring program.
   b. Newly Diagnosed Patients with office BP readings equal to or greater than 140/90 mmHg
      i. If the MEAN home BP is under 135/85 mmHg (<130/80 mmHg for diabetics and kidney disease): The patient is considered to have a normal BP and may be monitored for 8 days (similar to first week screening method) once every 2 months until end of the program, and followed up with by the Nurse practitioner once a month
      ii. If the MEAN home BP is equal to or greater than 135/85 mmHg: Hypertension is confirmed and the patient is enrolled into the full monitoring program
3. Full Monitoring Program: Patients confirmed with Hypertension may require an appointment with their Primary Care Physician for treatment
   a. Patients do not need to have their home BP monitored until after they are seen by their physician
   b. After the appointment, the Nurse practitioner should ensure that the details of the Primary Care Physician's treatment plan are entered into the service provider website and that the patient begins to monitor themselves MON WED FRI once between 6-10 AM and once between 6-10 PM each day (it does not matter if a day is missed, or the wrong day is measured for the purposes of the calculation of MEAN home BP)
   c. Fixed Follow-up Plan
      i. First 4 weeks of program, Nurse should contact patient once a week for "check-in" (takes 2-4 weeks for drug to take effect)
      ii. Following the first 4 weeks of the program, Nurse should contact the patient once every 2 weeks iii. At the midway point of the program; a reevaluation of the follow-up plan should take place to see if 2 weeks or 1 month will suffice for follow-up calls
iv. If one week's worth of readings is not taken, the Nurse practitioner should call the patient
v. Depending on compelling indications, the nurse can follow up with the patient more frequently if necessary
d. Every interaction by nurse practitioner with a patient or Primary Care Physician should require data entry into the website. The Nurse practitioner will have forms where she can enter all information gathered directly into the system. This information should include:
   a. Latest office BP reading taken (if any)
   b. Medication changes (type, dosage, frequency)
   c. Clinically significant symptoms/side effects that may affect management/treatment (this should be a free text window)
   d. Hospital visits
   e. Hospital admissions
   f. Emergency room visits
   g. Other notes regarding program from patient perspective
   h. MEDIC (office appointment schedule software)
e. The Nurse practitioner may monitor her schedule and readings through the IDEAL LIFE website
f. Monthly reports may be faxed to respective Primary Care Physicians (if able to, including medication changes)
g. Nurse practitioner should ensure that patients do not become alarmed about infrequent "out of range" measurements and should ensure that patient "issues" are addressed appropriately
4. If there are any "Out of Range" measurements, the nurse practitioner should call or otherwise contact the patient and make sure an appointment is made with their Primary Care Physician immediately (if the Primary Care Physician is unavailable, the patient should be seen by a specialist in the CCC or in the emergency room):
   a. Reading over 180/110 mmHg
   b. Reading under 100/60 mmHg
   c. Increase or decrease of more than 40/20 mmHg

APPENDIX C

Batch Processing
Nightly jobs will be run at 2 AM Pacific time. Each job must return its success or failure and notify the system administrator via email. The job should also create a log of the interactions created, in a text file, with file name "nightly job name and date".txt (e.g. FirstReadingCheck 15-JAN-2005.txt).
A nightly job will be run called FirstReadingCheck, checking each Our Partner Individual with a BP Manager . . . .
   1. If the patient does not yet have a registered BP Manager, then go to the next patient
   2. If the patient has a BP Manager with a registration_date < > null, and has readings, then go to the next patient
   3. If the registration_date is more than 24 hours before the current time, then create an interaction
      a. (interaction_typeID=1, interaction_purpose_ID=1024, interaction.auto-generated=8, interaction.comments="First Phase 1 reading not yet received.")
A second nightly job will be run called Phase1 to set the value of the Phase1 Values and the Hypertensive flag above, checking each Our Partner Individual with a BP Manager . . . .
   1. If the Phase1 Values for a patient are not null, then go to the next patient
   2. When the first reading from Our Partner Individual is received that has a reading date later than Jan. 1, 2004, set the Phase1 Start Date to the Reading Date. DO THIS ONLY ONCE—IF THE FIELD CONTAINS A VALUE DO NOT CHANGE IT.
   3. If the Phase 1 start date is null go to the next patient
   4. Check to see if the last 2 days are without readings. If so, create an interaction for the Nurse Practitioner.
      a. (interaction_typeID=1, interaction_purpose_ID=1024, interaction.auto-generated=1, interaction.comments="Two consecutive days of Phase 1 readings not received.")
   5. If the number of days elapsed since Phase1 start date is <9 the go to next patient
   6. Count the readings for Phase1 days 2 through 8 (i.e. Phase1 start date+1 through Phase1 start date+7), and if there are less than 10 readings, and not more than 2 days without readings, add an interaction for the Nurse practitioner to call the patient to restart taking readings, and reset the Phase1 Start Date for this user to Phase1 Start Date+1 day.
      a. (interaction_typeID=1, interaction_purpose_ID=1024, interaction.auto-generated=1, "Not enough readings to complete Phase 1 in last 7 days.")
   7. Calculate the average systolic, diastolic and heartrate for days 2 through 8 (i.e. Phase1 start date+1 through Phase1 start date+7), and store the values in Phase 1 Values above.
   8. If the MeanSystolic>=ThreshholdControlSystolic or MeanDiastolic>=ThreshholdControlDiastolic then set the Hypertensive flag=2
   9. If the Hypertensive flag=2, remove the Individual from the Normotensive static group and add them to the Hypertensive static group
   10. If Classification type=existing drug therapy AND MeanSystolic <ThreshholdMedicationControl the set the Hypertensive flag=3, remove the Individual from the Normotensive static group and add the Individual to the "Hypotensive suspect" static group
   11. Add records for the Phase 1 Fixed Follow-Up Plan below, depending on whether the patient is Hypertensive, Hypotensive, Hypotensive suspect, or Normotensive.
A third nightly job will be run called Phase2Startup to create the Fixed Followup Plan after the Nurse Practitioner enters the Phase 2 start date, checking each Our Partner Individual with a BP Manager . . . .
   1. If the Phase1 Values for a patient are null, then go to the next patient
   2. If the Phase2 start date is null then go to the next patient
   3. If the Phase 3 start date is not null then go to the next patient
   4. Add records for the Phase 2 Fixed Follow-Up Plan below, depending on whether the patient is Hypertensive or Hypotensive.
A fourth nightly job will be run called Phase2 to set the value of the Phase2 Values, and to start Phase3, checking each Our Partner Individual with a BP Manager . . . .
   1. If the Phase1 Values for a patient are null, then go to the next patient
   2. If the Phase2 start date is null, then go to the next patient
   3. If the Phase 3 start date is not null, go to the next patient
   4. If the current date is less than 183 days after the patient's program start date or the Phase2 Values are not null, then go to the next patient 5. Calculate the average systolic, diastolic and heartrate for days 177 through 183 (i.e. Phase2 start date+176 through Phase1 start date+182) and store the values in Phase2 Values above.
6. Update the Phase3 start date with the datetime of the nightly job
   a. (interaction_typeID=1, interaction_purpose_ID=1024, interaction.auto-generated=2, interaction.comments="Start twice daily monitoring for Phase 3.")

A fifth nightly job will be run called Phase3 to set the value of the Phase3 Values checking each Our Partner Individual with a BP Manager . . . .
1. If the Phase3 start date is null, then go to the next patient
2. If the Phase 4 start date is not null, then go to the next patient
3. Check to see if the last 2 days are without readings. If so, create an interaction for the Nurse Practitioner.
   a. (interaction_typeID=1, interaction_purpose_ID=1024, interaction.auto-generated=3, interaction.comments="Two consecutive days of Phase 3 readings not received.")
4. If the number of days elapsed since Phase3 start date is <9 the go to next patient
5. Count the readings for Phase3 days 2 through 8 (i.e. Phase3 start date+1 through Phase3 start date+7), and if there are less than 10 readings, and not more than 2 days without readings, add an interaction for the Nurse practitioner to call the patient to restart taking readings, and reset the Phase3 Start Date for this user to Phase3 Start Date+1 day.
   a. (interaction_typeID=1, interaction_purpose_ID=1024, interaction.auto-generated=3, "Not enough readings to complete Phase 3 in last 7 days.")
6. Calculate the average systolic, diastolic and heartrate for days 2 through 8 (i.e. Phase3 start date+1 through Phase3 start date+7), and store the values in Phase 3 Values above.
7. Add records for the Phase 3 Fixed Follow-Up Plan below, depending on whether the patient is Hypertensive, Hypotensive or Normotensive.

A sixth nightly job will be run called WeeklyReadingsCheck to determine if a patient has skipped a week of readings. If a patient has no readings for the entire previous week (7 days), and any of the Phase1 start date, Phase2 start date or Phase3 start dates are not null, then create an interaction for the Nurse Practitioner to call the patient (interaction_typeID=1, interaction_purpose_ID=1024, interaction.auto-generated=9, interaction.comments="One week of readings not received.").

Interactions
To track patient interactions the following will be included . . . .
1. Interaction
   a. interactionID
   b. interaction_typeID
   c. individualID
   d. professionalID
   e. Our Partner_interactionID
   f. interaction_date datetime
   g. duration datetime
   h. comments memo
   i. completed yes/no flag default=no (0)
   j. auto-generated values=1, 2, 3, 4, 8, 9, 99 or default=null 2. InteractionType
   a. Interaction_typeID
      i. Call to patient=1
      ii. Call to PCP=2
      iii. Call to Hospitalist=3
      iv. Call to Specialist=4
      v. Visit by professional to patient at home=10
      vi. Visit by professional to patient in hospital=11
      vii. Visit by patient to hospital=12
      viii. Visit by patient to hospital admission=13
      ix. Visit by patient to emergency room=14
      x. Visit by patient to lab/test facility=15
      xi. Fax report to PCP=20
      xii. Reminder=30
      xiii. Update records=40
   b. Description varchar(50)
      i. Values as above
3. InteractionPurpose
   a. Interaction_purposeID unsigned VERY long integer (64 bits) TBD
      i. Discuss BP Manager usage=1
      ii. Discuss general follow-up=2
      iii. Discuss out of range reading=4
      iv. Discuss change medication=8
      v. Discuss education=16
      vi. Discuss motivation=32
      vii. Schedule appointment with physician=64
      viii. Schedule appointment with hospitalist=128
      ix. Schedule appointment with specialist=256
      x. Schedule appointment with patient=512
      xi. Remind patient about monitoring=1024
      xii. Record PCP office visit details=2048
      xiii. Record symptoms/side effects=4096
      xiv. Record medication change=8192
      xv. Record diet change=16384
      xvi. Record hospital visit=32768
      xvii. Record hospital admission=65536
      xviii. Record emergency room visit=131072
      xix. Record patient hospital visit=262144
      xx. Record patient hospital admission=524288
      xxi. Record patient emergency room visit=1048576
      xxii. Record patient lab/test facility results=2097152
      xxiii. Provide monthly PCP report=4194304
      xxiv. Reset hypotensive suspect status=8388608
      xxv. Record patient history=16777216
      xxvi. Red Zone Alert threshold reading=33554432
      xxvii. Purple Zone Alert threshold reading=67108864
      xxviii. Yellow Zone Alert threshold reading=134217728
      xxix. Other=268435436
   b. Description varchar(50)
      i. Values as above ANDED together if more than one selected Followup Plans
1. Phase 1 Fixed Followup Plan (interactions created with nightly job Phase1)
   a. For Normotensive patients (Hypertensive flag=0) the following interactions will be created AUTOMATICALLY . . . .
      a. Set Phase2 start date=date of nightly job
      b. All interactions created below will have interaction.auto-generated=2 c. Normotensive patient monitoring reminders at Phase 2 date+60, +120, +180 days (interaction_typeID=1, interaction_purpose_ID=1024, comments="Remind normotensive patient to start 8 days of twice daily monitoring")

d. Fax report to PCP at program start date+9, +60, +120, +180 days (interaction_typeID=20, interaction_purpose_ID=4194304, comments="Fax patient report PCP")

b. For Hypertensive patients (Hypertensive flag=2) the following interactions will be created AUTOMATICALLY . . . .

a. All interactions created below will have interaction.auto-generated=1 b. Phone calls to Book PCP appointment dated at datetime of nightly job
    i. (interaction_typeID=2, interaction_purpose_ID=64, comments="Call PCP to book patient appointment")
    ii. (interaction_typeID=1, interaction_purpose_ID=512, comments="Call patient to book PCP appointment")

c. Update the details of the PCP visit (at nightly job date+4 days)
    i. (interaction_typeID=40, interaction_purpose_ID=2048, comments="Enter the details of patient's PCP appointment and set the Phase 2 start date")

c. For Hypotensive suspect patients (Hypertensive flag=3) the following interactions will be created AUTOMATICALLY . . . .

a. All interactions created below will have interaction.auto-generated=1 b. Phone calls to Book PCP appointment dated at datetime of nightly job
    i. (interaction_typeID=2, interaction_purpose_ID=64, comments="Call PCP to book patient appointment")
    ii. (interaction_typeID=1, interaction_purpose_ID=512, comments="Call patient to book PCP appointment")

c. Update the details of the PCP visit and reset Hypertensive flag Normotensive or Hypotensive after the PCP visit (at nightly job date+4 days)
    i. (interaction_typeID=40, interaction_purpose_ID=2048, comments="Enter the details of patient's PCP appointment and set the Phase 2 start date")
    ii. (interaction_typeID=40, interaction_purpose_ID=8388608, comments="Enter the new patient group status of either Normotensive or Hypotensive")

2. Phase 2 Fixed Followup Plan (interactions created with nightly job Phase2)

a. All Phase 2 interactions created with this Followup Plan will have interaction.auto-generated=2 b. For Normotensive patients (Hypertensive flag=0) the following interactions will be created AUTOMATICALLY (this will apply only for former "Hypotensive suspects" that the nurse changed to "Normotensive") . . . .

a. All interactions created below will have interaction.auto-generated=2 b. Normotensive patient monitoring reminders at Phase 2 date+60, +120, +180 days (interaction_typeID=1, interaction_purpose_ID=1024, comments="Remind normotensive patient to start 8 days of twice daily monitoring")

c. Fax report to PCP at program start date+9, +60, +90, +120, +150, +180 days (interaction_typeID=20, interaction_purpose_ID=4194304, comments="Fax patient report PCP")

c. For Hypertensive and Hypotensive patients (Hypertensive flag=1 or 2) the following interactions will be created AUTOMATICALLY . . . .

a. Recurring phone calls to patient for followup at Phase2 start date+7, +14, +21, +28, +42, +56, +70, +84, +98, +112, +126, +140, +154, +168, +182 days with multiple purposes
      i. (interaction_typeID=1, interaction_purpose_ID=63 i.e. Purposes (1, 2, 4, 8, 16, AND 32), comments="Scheduled patient followup call")

b. Fax report to PCP at program start date+30, +60, +120, +180 days
      i. (interaction_typeID=20, interaction_purpose_ID=4194304, comments="Fax patient report PCP")

3. End of Phase 3 Fixed Followup Plan (interactions created with nightly job Phase3)

a. All Phase 3 interactions created with this Followup Plan will have interaction.auto-generated=3 b. Fax report to PCP
    a. (interaction_typeID=20, interaction_purpose_ID=4194304, comments="Fax patient report PCP")

c. Phone calls to Book PCP appointment dated at datetime of nightly job
    a. (interaction_typeID=2, interaction_purpose_ID=64, comments="Call PCP to book patient appointment")
    b. (interaction_typeID=1, interaction_purpose_ID=512, comments="Call patient to book PCP appointment")

d. Update the details of the PCP visit (at nightly job date+4 days)
    a. (interaction_typeID=40, interaction_purpose_ID=2048, comments="Enter the details of patient's PCP appointment")

4. Phase 4 Fixed Followup Plan (interactions created with nightly job Phase4)

a. All Phase 4 interactions created with this Followup Plan will have interaction.auto-generated=4 b. Content TBD

Threshholds

Threshholds will be created automatically for each patient . . . .

1. Red Zone for readings greater than 180 systolic or 110 diastolic
2. Purple Zone for readings less than 100 systolic or 60 diastolic
3. Yellow Zone for readings with an absolute value change greater than or equal to 40 systolic or 20 diastolic Alerts Email alerts will be sent automatically to the Nurse Practitioner for the following (we will also attach alerts to other communication media)

1. Red Zone threshold readings
2. Purple Zone threshold readings
3. Yellow Zone threshold readings When an alert is generated it will also generate the following interactions . . . .

1. All interactions created below will have interaction.auto-generated=99

2. Phone call to the patient for threshold alert followup (one of the following depending on alert type) . . . .
   a. (interaction_typeID=1, interaction_purpose_ID= 33554432, comments="Red Zone Alert Followup—Systolic greater than 180 or diastolic greater than 110")
   b. (interaction_typeID=1, interaction_purpose_ID= 67108864, comments="Purple Zone Alert Followup—Systolic less than 100 or diastolic less than 60")
   c. (interaction_typeID=1, interaction_purpose_ID= 134217728, comments="Yellow Zone Alert Followup—Systolic change greater than 40 or diastolic change greater than 20")
3. Phone call to the PCP for threshold alert followup (one of the following depending on alert type) . . . .
   a. (interaction_typeID=2, interaction_purpose_ID= 33554432, comments="Red Zone Alert Followup—Systolic greater than 180 or diastolic greater than 110—CALL PCP (IF IS PCP UNAVAILABLE ENSURE PATIENT IS SEEN BY HOSPITALIST IN CCC OR ER)")
   b. (interaction_typeID=2, interaction_purpose_ID= 367108864, comments="Purple Zone Alert Followup—Systolic less than 100 or diastolic less than 60—CALL PCP (IF IS PCP UNAVAILABLE ENSURE PATIENT IS SEEN BY HOSPITALIST IN CCC OR ER)")
   c. (interaction_typeID=2, interaction_purpose_ID= 134217728, comments="Yellow Zone Alert Followup—Systolic change greater than 40 or diastolic change greater than 20—CALL PCP (IF IS PCP UNAVAILABLE ENSURE PATIENT IS SEEN BY HOSPITALIST IN CCC OR ER)")
4. Update the outcome(s) of the earlier alert . . . .
   a. (interaction_typeID=40, interaction_purpose_ID= 4192256 i.e. Purposes (4096 through 2097152, ANDED), comments="Enter the outcome(s) of the earlier alert—visit/admission/medication etc.")

Web Pages

The Professional role web pages used by the Nurse Practitioner will include the Project Dashboard, with a summary of groups, patient type, alerts and interactions, with current counts. Selecting a group will bring up a hyperlinked list of all patients in the group. Hyperlinks will also lead to other sections that include: Readings, Alerts, Interactions, Medications, Patient Groups, Office BP and Reports.

The Readings page will offer the standard set of existing charts.

The Alerts page will show all alerts for a patient, completed/not completed/all (default=not completed). A hyperlinked list of interactions will expand one interaction to show all detail and permit editing. Completed alerts can be ticked and removed with the Submit button.

The Interactions page will show all interactions for a patient, completed/not completed/all (default=not completed). A hyperlinked list of interactions will expand one interaction to show all detail and permit editing. Completed interactions can be ticked and removed with the Submit button. Also, the user will be able to enter a new interaction on the same page separate page.

The Pharmacy page will show the pharmacy records for the patient, uploaded monthly from Our Partner The Medications page will show new medications entered between pharmacy uploads for the patient, permit entry of a new medications and reconciliation with pharmacy records. (Reconciliation will also be automated)

The Office BP page will show a list of all Office BP readings for a patient, and permit entry of new readings.

The Reports page will show the standard report to be faxed to the PCP, and a print button will print the cover page and report for faxing offline. (we will log with time and date stamps every time the print button is clicked on, so that we can create a monitoring mechanism for faxes to be sent; we will also create a button for auto faxing—this feature will not require the nurse practitioner to manually fax the printed report but the database will automatically send out the fax from a the fax server).

The Contact Center role web pages used by the Nurse Practitioner will be customized for Our Partner patient data, and will provide the ability to enter or edit data for patients, and to register or change registration of BP Managers.

The invention claimed is:

1. A method for managing health comprising:

establishing, with the aid of at least one computer, one or more groups, each of which to include a plurality of persons, each group being established based on at least one of a plurality of health-related concerns that is capable of being monitored with respect to a person by a portable monitoring device which is capable of (i) transmitting physiological measurement data obtained from the person related to the at least one of the plurality of health-related concerns for delivery to the at least one computer and (ii) displaying a message transmitted by the at least one computer that is received by the monitoring device;

associating, with the aid of the at least one computer, each established group with at least one of the plurality of health-related concerns;

assigning, with the aid of the at least one computer, respective persons to an established group based on health-related information of the respective persons relating to the at least one of the plurality of health-related concerns associated with the respective group including initial physiological measurement data obtained from the respective persons satisfying at least one criterion;

assigning, with the aid of the at least one computer, a respective monitoring device to respective persons assigned to each respective established group based on the at least one health-related concern with which the respective group is associated;

storing in a data storage device accessible by the at least one computer information uniquely identifying each person in each established group;

transmitting for delivery to the monitoring device of at least one person in at least one established group, by the at least one computer, a message applicable to the health-related concern related to the at least one established group using the information uniquely identifying the at least one person in the at least one established group and the association of the at least one person with the at least one established group, the message comprising one or more of text, numbers and graphical images of one or more of health related news, health related data, alerts and advertising related to the at least one health-related concern of the at least one established group;

receiving, by the at least one monitoring device, the message transmitted by the at least one computer for delivery thereto;

displaying, by the at least one monitoring device, the message received by the at least one monitoring device;

receiving, over a network, at the at least one computer, respective subsequent physiological measurement data of respective persons in each established group, the respective subsequent physiological measurement data being provided by respective monitoring devices in association with the information uniquely identifying the respective persons in each established group, the respective subsequent data being received at the at least one computer after receipt of the respective initial measurement data of the respective persons;

storing the received subsequent physiological measurement data in a storage device accessible by the at least one computer in association with the respective person identified by the received identifying information; and changing, with the aid of the at least one computer, the group assignment of at least one of the respective persons based on the subsequent physiological measurement data received by the at least one computer of the at least one of the respective persons and the at least one criterion.

2. The method of claim 1 further comprising identifying, by the at least one computer, a person in an established group as a candidate for possible intervention based on the received subsequent physiological measurement data of the person and stored information applicable to a health-related concern related to the established group of which the person is a member.

3. The method of claim 2 comprising contacting an identified person or a representative thereof when a determination has been made to intervene with respect to that identified person.

4. The method of claim 3 wherein contacting comprises providing the identified person or representative with an electronically delivered message.

5. The method of claim 3 wherein contacting comprises a person contacting the identified person or representative by telephone.

6. The method of claim 3 wherein contacting comprises a person not a doctor contacting the identified person.

7. The method of claim 3 wherein contacting comprises a health care professional contacting the identified person.

8. The method of claim 2 further comprising the at least one computer automatically determining whether to intervene based on the stored information accessible, by the at least one computer, related to the identified person.

9. The method of claim 2 further comprising reviewing, by a person, stored information accessible by the at least one computer related to the identified person before a determination is made as to whether to intervene.

* * * * *